US006051553A

United States Patent [19]
Horwitz

[11] Patent Number: 6,051,553
[45] Date of Patent: *Apr. 18, 2000

[54] METHOD FOR POTENTIATING BPI PROTEIN PRODUCT BACTERICIDAL ACTIVITY BY ADMINISTRATION OF LBP PROTEIN PRODUCTS

[75] Inventor: Arnold Horwitz, Los Angeles, Calif.

[73] Assignee: Xoma Corporation, Berkeley, Calif.

[*] Notice: This patent is subject to a terminal disclaimer.

[21] Appl. No.: 09/102,325

[22] Filed: Jun. 22, 1998

Related U.S. Application Data

[63] Continuation of application No. 08/274,303, Jul. 11, 1994, Pat. No. 5,770,561, which is a continuation-in-part of application No. 08/093,201, Jul. 14, 1993, abandoned.

[51] Int. Cl.[7] .......................... A61K 38/16; A61K 38/00; C07K 1/00
[52] U.S. Cl. ................. 514/8; 514/12; 514/14; 514/152; 514/192; 530/350
[58] Field of Search .................. 514/8, 12, 14, 514/21, 152, 192; 530/350

[56] References Cited

U.S. PATENT DOCUMENTS

| | | |
|---|---|---|
| 5,089,274 | 2/1992 | Marra et al. . |
| 5,171,739 | 12/1992 | Scott . |
| 5,198,541 | 3/1993 | Elsbach et al. . |
| 5,234,912 | 8/1993 | Marra et al. . |
| 5,308,834 | 5/1994 | Scott et al. . |
| 5,334,584 | 8/1994 | Scott et al. . |
| 5,348,942 | 9/1994 | Little, II et al. . |

FOREIGN PATENT DOCUMENTS

| | | |
|---|---|---|
| WO 92/03535 | 3/1992 | WIPO . |
| WO 92/09621 | 6/1992 | WIPO . |
| WO 93/06228 | 4/1993 | WIPO . |
| WO 93/23434 | 11/1993 | WIPO . |
| WO 93/23540 | 11/1993 | WIPO . |
| WO 94/17819 | 8/1994 | WIPO . |
| WO 94/18323 | 8/1994 | WIPO . |
| WO 94/20128 | 9/1994 | WIPO . |
| WO 94/20129 | 9/1994 | WIPO . |
| WO 94/20532 | 9/1994 | WIPO . |

OTHER PUBLICATIONS

Saunders et al., International journal of antimicrobial agents (1995), vol. 5 No. 4.( abstract only), 1995.

Elsbach et al., "Separation and Purification of a Potent Bactericidal/Permeability–Increasing Protein and a Closely Associated Phospholipase $A_2$ from Rabbit Polymorphonuclear Leukocytes", *J. Biol. Chem.*, 254(21):11000–11009 ( Nov. 10, 1979).

Elsbach and Weiss, "Oxygen–Independent Antimicrobial Systems of Phagocytes", *Inflammation: Basic Principles and Clinical Correlates*, eds. Gallin et al., Chapter 30, Review Press, Ltd. (1992).

Gazzano–Santoro et al., "High–Affinity Binding of the Bactericidal/Permeability–Increasing Protein and a Recombinant Amino–Terminal Fragment to the Lipid A Region of Lipopolysaccharide", *Infect. Immun.*, 60(11):4754–4761 (Nov. 1992).

Gray et al., "Cloning of the cDNA of a Human Neutrophil Bactericidal Protein", *J. Biol. Chem.*, 264(16):9505–9509 (Jun. 5, 1989).

Levy et al., "Antibacterial 15–kDa Protein Isoforms (p15s) Are Members of a Novel Family of Leukocyte Proteins", *J. Biol. Chem.*, 268(8):6058–6068 (Mar. 16, 1993).

Mannion et al., "Preferential Binding of the Neutrophil Cytoplasmic Granule–Derived Bactericidal/Permeability Increasing Protein to Target Bacteria", *J. Clin. Invest.*, 142(8):2807–2812 (Apr. 15, 1989).

Mannion et al., "Separation of Sublethal and Lethal Effects of the Bactericidal/Permeability Increasing Protein on *Escheria coli*", *J. Clin. Invest.*, 85:853–860 (Mar. 1990).

Mannion et al., "Separation of Sublethal and Lethal Effects of Polymorphonuclear Leukocytes on *Escheria coli*", *J. Clin. Invest.*, 86:631–641 (Aug. 1990).

Marra et al., "The Role of Bactericidal/Permeability–Increasing Protein as a Natural Inhibitor of Bacterial Endotoxin", *J. Immunol.* 148(2):532–537 (Jan. 15, 1992).

Ooi et al., "Endotoxin–neutralizing Properties of the 25 kD N–Terminal Fragment and a Newly Isolated 30 kD C–Terminal Fragment of the 55–60 kD Bactericidal/Permeability–increasing Protein of Human Neutrophils", *J. Exp. Med.*, 174:649–655 (Sep. 1991).

Ooi et al., "A 25–kDa $NH_2$–terminal Fragment Carries all the Antibacterial Activities of the Human Neutrophil 60–kDa Bactericidal/Permeability–increasing Protein", *J. Biol. Chem.*, 262(31):1481–14894 (1987).

Schumann et al., "Structure and Function of Lipopolysaccharide Binding Protein", *Science*, 249:1429–1431 (Sep. 21, 1990).

Tobias et al., "Participation of Lipopolysaccharide–binding Protein in Lipopolysaccharide–dependant Macrophage Activation", *Am. J. Resp. Cell. Mol. Biol.*, 7:239–245 (1992).

Ulevitch et al., "A New Model of Macrophage Stimulation by Bacterial Lipopolysaccharide", *Advances in Understanding Trauma and Burn Injury*, 30(12):S189–S192 (Dec. 1990).

Weiss et al., "Resistance of Gram–negative Bacteria to Purified Bactericidal Leukocyte Proteins", *J. Clin. Invest.* 65:619–628 (Mar. 1980).

(List continued on next page.)

*Primary Examiner*—Keith D. MacMillan
*Assistant Examiner*—P. Ponnaluri
*Attorney, Agent, or Firm*—Marshall, O'Toole, Gerstein, Murray & Borun

[57] ABSTRACT

The present invention provides methods of potentiating the gram-negative bactericidal activity of BPI protein products by means of administering LBP protein products.

21 Claims, 18 Drawing Sheets

OTHER PUBLICATIONS

Weiss et al., "Cellular and Subcellular Localization of the Bactericidal/Permeability–Increasing Protein of Neutrophils", *Blood*, 69(2):652–659 (Feb. 1987).

Weiss et al., "Human Bactericidal/Permeability–increasing Protein and a Recombinant $NH_2$–Terminal Fragment Cause Killing of Serum–resistant Gram–negative Bacteria in Whole Blood and Inhibit Tumor Necrosis Factor Release Induced by the Bacteria", *J. Clin. Invest.*, 90:1122–1130 (Sep. 1992).

Wright et al., "CD14, a Receptor for Complexes of Lipopolysaccharide (LPS) and LPS Binding Protein", *Science*, 249:1431–1433 (Sep. 21, 1990).

Heumann et al., "Competition between Bactericidal/Permeability–Increasing Protein and Lipopolysaccharide–Binding Protein for Lipopolysaccharide Binding to Monocytes", *J. Infectious Diseases*, 167(6):1351–1357 (Jun. 1993).

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
        (A) LENGTH: 1813 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 31..1491

(ix) FEATURE:
        (A) NAME/KEY: mat_peptide
        (B) LOCATION: 124..1491

(ix) FEATURE:
        (A) NAME/KEY: misc_feature
        (D) OTHER INFORMATION: "rBPI"

(xi) SEQUENCE DESCRIPTION: SEQ ID NO:1:

```
CAGGCCTTGA GGTTTTGGCA GCTCTGGAGG ATG AGA GAG AAC ATG GCC AGG GGC          54
                                 Met Arg Glu Asn Met Ala Arg Gly
                                 -31 -30                     -25

CCT TGC AAC GCG CCG AGA TGG GTG TCC CTG ATG GTG CTC GTC GCC ATA          102
Pro Cys Asn Ala Pro Arg Trp Val Ser Leu Met Val Leu Val Ala Ile
            -20             -15                 -10

GGC ACC GCC GTG ACA GCG GCC GTC AAC CCT GGC GTC GTG GTC AGG ATC          150
Gly Thr Ala Val Thr Ala Ala Val Asn Pro Gly Val Val Val Arg Ile
        -5                   1               5

TCC CAG AAG GGC CTG GAC TAC GCC AGC CAG CAG GGG ACG GCC GCT CTG          198
Ser Gln Lys Gly Leu Asp Tyr Ala Ser Gln Gln Gly Thr Ala Ala Leu
10              15                  20                  25

CAG AAG GAG CTG AAG AGG ATC AAG ATT CCT GAC TAC TCA GAC AGC TTT          246
Gln Lys Glu Leu Lys Arg Ile Lys Ile Pro Asp Tyr Ser Asp Ser Phe
                30                  35                  40

AAG ATC AAG CAT CTT GGG AAG GGG CAT TAT AGC TTC TAC AGC ATG GAC          294
Lys Ile Lys His Leu Gly Lys Gly His Tyr Ser Phe Tyr Ser Met Asp
                45                  50                  55

ATC CGT GAA TTC CAG CTT CCC AGT TCC CAG ATA AGC ATG GTG CCC AAT          342
Ile Arg Glu Phe Gln Leu Pro Ser Ser Gln Ile Ser Met Val Pro Asn
        60                  65                  70

GTG GGC CTT AAG TTC TCC ATC AGC AAC GCC AAT ATC AAG ATC AGC GGG          390
Val Gly Leu Lys Phe Ser Ile Ser Asn Ala Asn Ile Lys Ile Ser Gly
    75                  80                  85

AAA TGG AAG GCA CAA AAG AGA TTC TTA AAA ATG AGC GGC AAT TTT GAC          438
Lys Trp Lys Ala Gln Lys Arg Phe Leu Lys Met Ser Gly Asn Phe Asp
90                  95                  100                 105

CTG AGC ATA GAA GGC ATG TCC ATT TCG GCT GAT CTG AAG CTG GGC AGT          486
Leu Ser Ile Glu Gly Met Ser Ile Ser Ala Asp Leu Lys Leu Gly Ser
                110                 115                 120

AAC CCC ACG TCA GGC AAG CCC ACC ATC ACC TGC TCC AGC TGC AGC AGC          534
Asn Pro Thr Ser Gly Lys Pro Thr Ile Thr Cys Ser Ser Cys Ser Ser
            125                 130                 135

CAC ATC AAC AGT GTC CAC GTG CAC ATC TCA AAG AGC AAA GTC GGG TGG          582
His Ile Asn Ser Val His Val His Ile Ser Lys Ser Lys Val Gly Trp
        140                 145                 150

CTG ATC CAA CTC TTC CAC AAA AAA ATT GAG TCT GCG CTT CGA AAC AAG          630
Leu Ile Gln Leu Phe His Lys Lys Ile Glu Ser Ala Leu Arg Asn Lys
    155                 160                 165

ATG AAC AGC CAG GTC TGC GAG AAA GTG ACC AAT TCT GTA TCC TCC AAG          678
Met Asn Ser Gln Val Cys Glu Lys Val Thr Asn Ser Val Ser Ser Lys
170                 175                 180                 185
```

```
CTG CAA CCT TAT TTC CAG ACT CTG CCA GTA ATG ACC AAA ATA GAT TCT        726
Leu Gln Pro Tyr Phe Gln Thr Leu Pro Val Met Thr Lys Ile Asp Ser
            190                 195                 200

GTG GCT GGA ATC AAC TAT GGT CTG GTG GCA CCT CCA GCA ACC ACG GCT        774
Val Ala Gly Ile Asn Tyr Gly Leu Val Ala Pro Pro Ala Thr Thr Ala
            205                 210                 215

GAG ACC CTG GAT GTA CAG ATG AAG GGG GAG TTT TAC AGT GAG AAC CAC        822
Glu Thr Leu Asp Val Gln Met Lys Gly Glu Phe Tyr Ser Glu Asn His
            220                 225                 230

CAC AAT CCA CCT CCC TTT GCT CCA CCA GTG ATG GAG TTT CCC GCT GCC        870
His Asn Pro Pro Pro Phe Ala Pro Pro Val Met Glu Phe Pro Ala Ala
        235                 240                 245

CAT GAC CGC ATG GTA TAC CTG GGC CTC TCA GAC TAC TTC TTC AAC ACA        918
His Asp Arg Met Val Tyr Leu Gly Leu Ser Asp Tyr Phe Phe Asn Thr
250                 255                 260                 265

GCC GGG CTT GTA TAC CAA GAG GCT GGG GTC TTG AAG ATG ACC CTT AGA        966
Ala Gly Leu Val Tyr Gln Glu Ala Gly Val Leu Lys Met Thr Leu Arg
            270                 275                 280

GAT GAC ATG ATT CCA AAG GAG TCC AAA TTT CGA CTG ACA ACC AAG TTC       1014
Asp Asp Met Ile Pro Lys Glu Ser Lys Phe Arg Leu Thr Thr Lys Phe
            285                 290                 295

TTT GGA ACC TTC CTA CCT GAG GTG GCC AAG AAG TTT CCC AAC ATG AAG       1062
Phe Gly Thr Phe Leu Pro Glu Val Ala Lys Lys Phe Pro Asn Met Lys
            300                 305                 310

ATA CAG ATC CAT GTC TCA GCC TCC ACC CCG CCA CAC CTG TCT GTG CAG       1110
Ile Gln Ile His Val Ser Ala Ser Thr Pro Pro His Leu Ser Val Gln
        315                 320                 325

CCC ACC GGC CTT ACC TTC TAC CCT GCC GTG GAT GTC CAG GCC TTT GCC       1158
Pro Thr Gly Leu Thr Phe Tyr Pro Ala Val Asp Val Gln Ala Phe Ala
330                 335                 340                 345

GTC CTC CCC AAC TCC TCC CTG GCT TCC CTC TTC CTG ATT GGC ATG CAC       1206
Val Leu Pro Asn Ser Ser Leu Ala Ser Leu Phe Leu Ile Gly Met His
            350                 355                 360

ACA ACT GGT TCC ATG GAG GTC AGC GCC GAG TCC AAC AGG CTT GTT GGA       1254
Thr Thr Gly Ser Met Glu Val Ser Ala Glu Ser Asn Arg Leu Val Gly
            365                 370                 375

GAG CTC AAG CTG GAT AGG CTG CTC CTG GAA CTG AAG CAC TCA AAT ATT       1302
Glu Leu Lys Leu Asp Arg Leu Leu Leu Glu Leu Lys His Ser Asn Ile
            380                 385                 390

GGC CCC TTC CCG GTT GAA TTG CTG CAG GAT ATC ATG AAC TAC ATT GTA       1350
Gly Pro Phe Pro Val Glu Leu Leu Gln Asp Ile Met Asn Tyr Ile Val
395                 400                 405

CCC ATT CTT GTG CTG CCC AGG GTT AAC GAG AAA CTA CAG AAA GGC TTC       1398
Pro Ile Leu Val Leu Pro Arg Val Asn Glu Lys Leu Gln Lys Gly Phe
410                 415                 420                 425

CCT CTC CCG ACG CCG GCC AGA GTC CAG CTC TAC AAC GTA GTG CTT CAG       1446
Pro Leu Pro Thr Pro Ala Arg Val Gln Leu Tyr Asn Val Val Leu Gln
            430                 435                 440

CCT CAC CAG AAC TTC CTG CTG TTC GGT GCA GAC GTT GTC TAT AAA           1491
Pro His Gln Asn Phe Leu Leu Phe Gly Ala Asp Val Val Tyr Lys
            445                 450                 455

TGAAGGCACC AGGGGTGCCG GGGGCTGTCA GCCGCACCTG TTCCTGATGG GCTGTGGGGC     1551

ACCGGCTGCC TTTCCCCAGG GAATCCTCTC CAGATCTTAA CCAAGAGCCC CTTGCAAACT     1611

TCTTCGACTC AGATTCAGAA ATGATCTAAA CACGAGGAAA CATTATTCAT TGGAAAAGTG     1671

CATGGTGTGT ATTTTAGGGA TTATGAGCTT CTTTCAAGGG CTAAGGCTGC AGAGATATTT     1731

CCTCCAGGAA TCGTGTTTCA ATTGTAACCA AGAAATTTCC ATTTGTGCTT CATGAAAAAA     1791

AACTTCTGGT TTTTTTCATG TG                                              1813
```

(2) INFORMATION FOR SEQ ID NO:2:

(i) SEQUENCE CHARACTERISTICS:
        (A) LENGTH: 487 amino acids
        (B) TYPE: amino acid
        (D) TOPOLOGY: linear (ii) MOLECULE TYPE: protein (xi) SEQUENCE DESCRIPTION: SEQ ID NO:2:

```
Met Arg Glu Asn Met Ala Arg Gly Pro Cys Asn Ala Pro Arg Trp Val
-31 -30             -25                 -20

Ser Leu Met Val Leu Val Ala Ile Gly Thr Ala Val Thr Ala Ala Val
-15             -10                  -5                       1

Asn Pro Gly Val Val Val Arg Ile Ser Gln Lys Gly Leu Asp Tyr Ala
                 5                  10                  15

Ser Gln Gln Gly Thr Ala Ala Leu Gln Lys Glu Leu Lys Arg Ile Lys
             20                  25                  30

Ile Pro Asp Tyr Ser Asp Ser Phe Lys Ile Lys His Leu Gly Lys Gly
         35                  40                  45

His Tyr Ser Phe Tyr Ser Met Asp Ile Arg Glu Phe Gln Leu Pro Ser
 50              55                  60                      65

Ser Gln Ile Ser Met Val Pro Asn Val Gly Leu Lys Phe Ser Ile Ser
                 70                  75                  80

Asn Ala Asn Ile Lys Ile Ser Gly Lys Trp Lys Ala Gln Lys Arg Phe
             85                  90                  95

Leu Lys Met Ser Gly Asn Phe Asp Leu Ser Ile Glu Gly Met Ser Ile
            100                 105                 110

Ser Ala Asp Leu Lys Leu Gly Ser Asn Pro Thr Ser Gly Lys Pro Thr
            115                 120                 125

Ile Thr Cys Ser Ser Cys Ser Ser His Ile Asn Ser Val His Val His
130             135                 140                     145

Ile Ser Lys Ser Lys Val Gly Trp Leu Ile Gln Leu Phe His Lys Lys
                150                 155                 160

Ile Glu Ser Ala Leu Arg Asn Lys Met Asn Ser Gln Val Cys Glu Lys
            165                 170                 175

Val Thr Asn Ser Val Ser Ser Lys Leu Gln Pro Tyr Phe Gln Thr Leu
            180                 185                 190

Pro Val Met Thr Lys Ile Asp Ser Val Ala Gly Ile Asn Tyr Gly Leu
            195                 200                 205

Val Ala Pro Pro Ala Thr Thr Ala Glu Thr Leu Asp Val Gln Met Lys
210             215                 220                     225

Gly Glu Phe Tyr Ser Glu Asn His His Asn Pro Pro Phe Ala Pro
                230                 235                 240

Pro Val Met Glu Phe Pro Ala Ala His Asp Arg Met Val Tyr Leu Gly
            245                 250                 255

Leu Ser Asp Tyr Phe Phe Asn Thr Ala Gly Leu Val Tyr Gln Glu Ala
            260                 265                 270

Gly Val Leu Lys Met Thr Leu Arg Asp Asp Met Ile Pro Lys Glu Ser
275             280                 285

Lys Phe Arg Leu Thr Thr Lys Phe Phe Gly Thr Phe Leu Pro Glu Val
290             295                 300                     305

Ala Lys Lys Phe Pro Asn Met Lys Ile Gln Ile His Val Ser Ala Ser
                310                 315                 320
```

```
Thr Pro Pro His Leu Ser Val Gln Pro Thr Gly Leu Thr Phe Tyr Pro
            325                 330                 335

Ala Val Asp Val Gln Ala Phe Ala Val Leu Pro Asn Ser Ser Leu Ala
            340                 345                 350

Ser Leu Phe Leu Ile Gly Met His Thr Thr Gly Ser Met Glu Val Ser
        355                 360                 365

Ala Glu Ser Asn Arg Leu Val Gly Glu Leu Lys Leu Asp Arg Leu Leu
370                 375                 380                 385

Leu Glu Leu Lys His Ser Asn Ile Gly Pro Phe Pro Val Glu Leu Leu
                390                 395                 400

Gln Asp Ile Met Asn Tyr Ile Val Pro Ile Leu Val Leu Pro Arg Val
            405                 410                 415

Asn Glu Lys Leu Gln Lys Gly Phe Pro Leu Pro Thr Pro Ala Arg Val
            420                 425                 430

Gln Leu Tyr Asn Val Val Leu Gln Pro His Gln Asn Phe Leu Leu Phe
        435                 440                 445

Gly Ala Asp Val Val Tyr Lys
450                 455
```

(2) INFORMATION FOR SEQ ID NO:3:

(i) SEQUENCE CHARACTERISTICS:
        (A) LENGTH: 591 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 1..591

(ix) FEATURE:
        (A) NAME/KEY: misc_feature
        (D) OTHER INFORMATION: "rLBP25"

(xi) SEQUENCE DESCRIPTION: SEQ ID NO:3:

```
GCC AAC CCC GGC TTG GTC GCC AGG ATC ACC GAC AAG GGA CTG CAG TAT      48
Ala Asn Pro Gly Leu Val Ala Arg Ile Thr Asp Lys Gly Leu Gln Tyr
 1               5                  10                  15

GCG GCC CAG GAG GGG CTA TTG GCT CTG CAG AGT GAG CTG CTC AGG ATC      96
Ala Ala Gln Glu Gly Leu Leu Ala Leu Gln Ser Glu Leu Leu Arg Ile
                20                  25                  30

ACG CTG CCT GAC TTC ACC GGG GAC TTG AGG ATC CCC CAC GTC GGC CGT     144
Thr Leu Pro Asp Phe Thr Gly Asp Leu Arg Ile Pro His Val Gly Arg
            35                  40                  45

GGG CGC TAT GAG TTC CAC AGC CTG AAC ATC CAC AGC TGT GAG CTG CTT     192
Gly Arg Tyr Glu Phe His Ser Leu Asn Ile His Ser Cys Glu Leu Leu
        50                  55                  60

CAC TCT GCG CTG AGG CCT GTC CCT GGC CAG GGC CTG AGT CTC AGC ATC     240
His Ser Ala Leu Arg Pro Val Pro Gly Gln Gly Leu Ser Leu Ser Ile
 65                 70                  75                  80

TCC GAC TCC TCC ATC CGG GTC CAG GGC AGG TGG AAG GTG CGC AAG TCA     288
Ser Asp Ser Ser Ile Arg Val Gln Gly Arg Trp Lys Val Arg Lys Ser
                85                  90                  95

TTC TTC AAA CTA CAG GGC TCC TTT GAT GTC AGT GTC AAG GGC ATC AGC     336
Phe Phe Lys Leu Gln Gly Ser Phe Asp Val Ser Val Lys Gly Ile Ser
                100                 105                 110

ATT TCG GTC AAC CTC CTG TTG GGC AGC GAG TCC TCC GGG AGG CCC ACA     384
Ile Ser Val Asn Leu Leu Leu Gly Ser Glu Ser Ser Gly Arg Pro Thr
            115                 120                 125
```

```
GTT ACT GCC TCC AGC TGC AGC AGT GAC ATC GCT GAC GTG GAG GTG GAC        432
Val Thr Ala Ser Ser Cys Ser Ser Asp Ile Ala Asp Val Glu Val Asp
    130                 135                 140

ATG TCG GGA GAC TTG GGG TGG CTG TTG AAC CTC TTC CAC AAC CAG ATT        480
Met Ser Gly Asp Leu Gly Trp Leu Leu Asn Leu Phe His Asn Gln Ile
145                 150                 155                 160

GAG TCC AAG TTC CAG AAA GTA CTG GAG AGC AGG ATT TGC GAA ATG ATC        528
Glu Ser Lys Phe Gln Lys Val Leu Glu Ser Arg Ile Cys Glu Met Ile
                165                 170                 175

CAG AAA TCG GTG TCC TCC GAT CTA CAG CCT TAT CTC CAA ACT CTG CCA        576
Gln Lys Ser Val Ser Ser Asp Leu Gln Pro Tyr Leu Gln Thr Leu Pro
            180                 185                 190

GTT ACA ACA GAG ATT                                                    591
Val Thr Thr Glu Ile
        195
```

(2) INFORMATION FOR SEQ ID NO:4:

(i) SEQUENCE CHARACTERISTICS:
        (A) LENGTH: 197 amino acids
        (B) TYPE: amino acid
        (D) TOPOLOGY: linear (ii) MOLECULE TYPE: protein (ix) FEATURE:
        (A) NAME/KEY: misc_feature
        (D) OTHER INFORMATION: "rLBP25"

(xi) SEQUENCE DESCRIPTION: SEQ ID NO:4:

```
Ala Asn Pro Gly Leu Val Ala Arg Ile Thr Asp Lys Gly Leu Gln Tyr
1               5                   10                  15

Ala Ala Gln Glu Gly Leu Leu Ala Leu Gln Ser Glu Leu Leu Arg Ile
            20                  25                  30

Thr Leu Pro Asp Phe Thr Gly Asp Leu Arg Ile Pro His Val Gly Arg
        35                  40                  45

Gly Arg Tyr Glu Phe His Ser Leu Asn Ile His Ser Cys Glu Leu Leu
    50                  55                  60

His Ser Ala Leu Arg Pro Val Pro Gly Gln Gly Leu Ser Leu Ser Ile
65                  70                  75                  80

Ser Asp Ser Ser Ile Arg Val Gln Gly Arg Trp Lys Val Arg Lys Ser
                85                  90                  95

Phe Phe Lys Leu Gln Gly Ser Phe Asp Val Ser Val Lys Gly Ile Ser
            100                 105                 110

Ile Ser Val Asn Leu Leu Leu Gly Ser Glu Ser Ser Gly Arg Pro Thr
        115                 120                 125

Val Thr Ala Ser Ser Cys Ser Ser Asp Ile Ala Asp Val Glu Val Asp
    130                 135                 140

Met Ser Gly Asp Leu Gly Trp Leu Leu Asn Leu Phe His Asn Gln Ile
145                 150                 155                 160

Glu Ser Lys Phe Gln Lys Val Leu Glu Ser Arg Ile Cys Glu Met Ile
                165                 170                 175

Gln Lys Ser Val Ser Ser Asp Leu Gln Pro Tyr Leu Gln Thr Leu Pro
            180                 185                 190

Val Thr Thr Glu Ile
        195
```

(2) INFORMATION FOR SEQ ID NO:5:

(i) SEQUENCE CHARACTERISTICS:
    (A) LENGTH: 1443 base pairs
    (B) TYPE: nucleic acid
    (C) STRANDEDNESS: single
    (D) TOPOLOGY: linear (ii) MOLECULE TYPE: DNA (ix) FEATURE:
    (A) NAME/KEY: CDS
    (B) LOCATION: 1..1443

(ix) FEATURE:
    (A) NAME/KEY: mat_peptide
    (B) LOCATION: 76..1443

(ix) FEATURE:
    (A) NAME/KEY: misc_feature
    (D) OTHER INFORMATION: "rLBP"

(xi) SEQUENCE DESCRIPTION: SEQ ID NO:5:

```
ATG GGG GCC TTG GCC AGA GCC CTG CCG TCC ATA CTG CTG GCA TTG CTG      48
Met Gly Ala Leu Ala Arg Ala Leu Pro Ser Ile Leu Leu Ala Leu Leu
-25             -20             -15                     -10

CTT ACG TCC ACC CCA GAG GCT CTG GGT GCC AAC CCC GGC TTG GTC GCC      96
Leu Thr Ser Thr Pro Glu Ala Leu Gly Ala Asn Pro Gly Leu Val Ala
                -5              1               5

AGG ATC ACC GAC AAG GGA CTG CAG TAT GCG GCC CAG GAG GGG CTA TTG     144
Arg Ile Thr Asp Lys Gly Leu Gln Tyr Ala Ala Gln Glu Gly Leu Leu
            10              15              20

GCT CTG CAG AGT GAG CTG CTC AGG ATC ACG CTG CCT GAC TTC ACC GGG     192
Ala Leu Gln Ser Glu Leu Leu Arg Ile Thr Leu Pro Asp Phe Thr Gly
25              30              35

GAC TTG AGG ATC CCC CAC GTC GGC CGT GGG CGC TAT GAG TTC CAC AGC     240
Asp Leu Arg Ile Pro His Val Gly Arg Gly Arg Tyr Glu Phe His Ser
40              45              50              55

CTG AAC ATC CAC AGC TGT GAG CTG CTT CAC TCT GCG CTG AGG CCT GTC     288
Leu Asn Ile His Ser Cys Glu Leu Leu His Ser Ala Leu Arg Pro Val
                60              65              70

CCT GGC CAG GGC CTG AGT CTC AGC ATC TCC GAC TCC TCC ATC CGG GTC     336
Pro Gly Gln Gly Leu Ser Leu Ser Ile Ser Asp Ser Ser Ile Arg Val
            75              80              85

CAG GGC AGG TGG AAG GTG CGC AAG TCA TTC TTC AAA CTA CAG GGC TCC     384
Gln Gly Arg Trp Lys Val Arg Lys Ser Phe Phe Lys Leu Gln Gly Ser
        90              95              100

TTT GAT GTC AGT GTC AAG GGC ATC AGC ATT TCG GTC AAC CTC CTG TTG     432
Phe Asp Val Ser Val Lys Gly Ile Ser Ile Ser Val Asn Leu Leu Leu
    105             110             115

GGC AGC GAG TCC TCC GGG AGG CCC ACA GTT ACT GCC TCC AGC TGC AGC     480
Gly Ser Glu Ser Ser Gly Arg Pro Thr Val Thr Ala Ser Ser Cys Ser
120             125             130             135

AGT GAC ATC GCT GAC GTG GAG GTG GAC ATG TCG GGA GAC TTG GGG TGG     528
Ser Asp Ile Ala Asp Val Glu Val Asp Met Ser Gly Asp Leu Gly Trp
            140             145             150

CTG TTG AAC CTC TTC CAC AAC CAG ATT GAG TCC AAG TTC CAG AAA GTA     576
Leu Leu Asn Leu Phe His Asn Gln Ile Glu Ser Lys Phe Gln Lys Val
        155             160             165

CTG GAG AGC AGG ATT TGC GAA ATG ATC CAG AAA TCG GTG TCC TCC GAT     624
Leu Glu Ser Arg Ile Cys Glu Met Ile Gln Lys Ser Val Ser Ser Asp
    170             175             180

CTA CAG CCT TAT CTC CAA ACT CTG CCA GTT ACA ACA GAG ATT GAC AGT     672
Leu Gln Pro Tyr Leu Gln Thr Leu Pro Val Thr Thr Glu Ile Asp Ser
185             190             195

TTC GCC GAC ATT GAT TAT AGC TTA GTG GAA GCC CCT CGG GCA ACA GCC     720
```

```
Phe Ala Asp Ile Asp Tyr Ser Leu Val Glu Ala Pro Arg Ala Thr Ala
200                 205                 210                 215

CAG ATG CTG GAG GTG ATG TTT AAG GGT GAA ATC TTT CAT CGT AAC CAC          768
Gln Met Leu Glu Val Met Phe Lys Gly Glu Ile Phe His Arg Asn His
            220                 225                 230

CGT TCT CCA GTT ACC CTC CTT GCT GCA GTC ATG AGC CTT CCT GAG GAA          816
Arg Ser Pro Val Thr Leu Leu Ala Ala Val Met Ser Leu Pro Glu Glu
                235                 240                 245

CAC AAC AAA ATG GTC TAC TTT GCC ATC TCG GAT TAT GTC TTC AAC ACG          864
His Asn Lys Met Val Tyr Phe Ala Ile Ser Asp Tyr Val Phe Asn Thr
            250                 255                 260

GCC AGC CTG GTT TAT CAT GAG GAA GGA TAT CTG AAC TTC TCC ATC ACA          912
Ala Ser Leu Val Tyr His Glu Glu Gly Tyr Leu Asn Phe Ser Ile Thr
        265                 270                 275

GAT GAG ATG ATA CCG CCT GAC TCT AAT ATC CGA CTG ACC ACC AAG TCC          960
Asp Glu Met Ile Pro Pro Asp Ser Asn Ile Arg Leu Thr Thr Lys Ser
280                 285                 290                 295

TTC CGA CCC TTC GTC CCA CGG TTA GCC AGG CTC TAC CCC AAC ATG AAC         1008
Phe Arg Pro Phe Val Pro Arg Leu Ala Arg Leu Tyr Pro Asn Met Asn
                300                 305                 310

CTG GAA CTC CAG GGA TCA GTG CCC TCT GCT CCG CTC CTG AAC TTC AGC         1056
Leu Glu Leu Gln Gly Ser Val Pro Ser Ala Pro Leu Leu Asn Phe Ser
            315                 320                 325

CCT GGG AAT CTG TCT GTG GAC CCC TAT ATG GAG ATA GAT GCC TTT GTG         1104
Pro Gly Asn Leu Ser Val Asp Pro Tyr Met Glu Ile Asp Ala Phe Val
        330                 335                 340

CTC CTG CCC AGC TCC AGC AAG GAG CCT GTC TTC CGG CTC AGT GTG GCC         1152
Leu Leu Pro Ser Ser Ser Lys Glu Pro Val Phe Arg Leu Ser Val Ala
345                 350                 355

ACT AAT GTG TCC GCC ACC TTG ACC TTC AAT ACC AGC AAG ATC ACT GGG         1200
Thr Asn Val Ser Ala Thr Leu Thr Phe Asn Thr Ser Lys Ile Thr Gly
360                 365                 370                 375

TTC CTG AAG CCA GGA AAG GTA AAA GTG GAA CTG AAA GAA TCC AAA GTT         1248
Phe Leu Lys Pro Gly Lys Val Lys Val Glu Leu Lys Glu Ser Lys Val
                380                 385                 390

GGA CTA TTC AAT GCA GAG CTG TTG GAA GCG CTC CTC AAC TAT TAC ATC         1296
Gly Leu Phe Asn Ala Glu Leu Leu Glu Ala Leu Leu Asn Tyr Tyr Ile
            395                 400                 405

CTT AAC ACC TTC TAC CCC AAG TTC AAT GAT AAG TTG GCC GAA GGC TTC         1344
Leu Asn Thr Phe Tyr Pro Lys Phe Asn Asp Lys Leu Ala Glu Gly Phe
        410                 415                 420

CCC CTT CCT CTG CTG AAG CGT GTT CAG CTC TAC GAC CTT GGG CTG CAG         1392
Pro Leu Pro Leu Leu Lys Arg Val Gln Leu Tyr Asp Leu Gly Leu Gln
425                 430                 435

ATC CAT AAG GAC TTC CTG TTC TTG GGT GCC AAT GTC CAA TAC ATG AGA         1440
Ile His Lys Asp Phe Leu Phe Leu Gly Ala Asn Val Gln Tyr Met Arg
440                 445                 450                 455

GTT                                                                     1443
Val
```

(2) INFORMATION FOR SEQ ID NO:6:

(i) SEQUENCE CHARACTERISTICS:
        (A) LENGTH: 481 amino acids
        (B) TYPE: amino acid
        (D) TOPOLOGY: linear (ii) MOLECULE TYPE: protein (ix) FEATURE:
        (A) NAME/KEY: misc_feature
        (D) OTHER INFORMATION: "rLBP"

(xi) SEQUENCE DESCRIPTION: SEQ ID NO:6:

```
Met Gly Ala Leu Ala Arg Ala Leu Pro Ser Ile Leu Ala Leu Leu
-25             -20             -15             -10

Leu Thr Ser Thr Pro Glu Ala Leu Gly Ala Asn Pro Gly Leu Val Ala
            -5                   1                5

Arg Ile Thr Asp Lys Gly Leu Gln Tyr Ala Ala Gln Glu Gly Leu Leu
        10              15              20

Ala Leu Gln Ser Glu Leu Leu Arg Ile Thr Leu Pro Asp Phe Thr Gly
        25              30              35

Asp Leu Arg Ile Pro His Val Gly Arg Gly Arg Tyr Glu Phe His Ser
40              45              50              55

Leu Asn Ile His Ser Cys Glu Leu Leu His Ser Ala Leu Arg Pro Val
                60              65              70

Pro Gly Gln Gly Leu Ser Leu Ser Ile Ser Asp Ser Ser Ile Arg Val
            75              80              85

Gln Gly Arg Trp Lys Val Arg Lys Ser Phe Phe Lys Leu Gln Gly Ser
        90              95              100

Phe Asp Val Ser Val Lys Gly Ile Ser Ile Ser Val Asn Leu Leu Leu
105             110             115

Gly Ser Glu Ser Ser Gly Arg Pro Thr Val Thr Ala Ser Ser Cys Ser
120             125             130             135

Ser Asp Ile Ala Asp Val Glu Val Asp Met Ser Gly Asp Leu Gly Trp
            140             145             150

Leu Leu Asn Leu Phe His Asn Gln Ile Glu Ser Lys Phe Gln Lys Val
            155             160             165

Leu Glu Ser Arg Ile Cys Glu Met Ile Gln Lys Ser Val Ser Ser Asp
        170             175             180

Leu Gln Pro Tyr Leu Gln Thr Leu Pro Val Thr Thr Glu Ile Asp Ser
        185             190             195

Phe Ala Asp Ile Asp Tyr Ser Leu Val Glu Ala Pro Arg Ala Thr Ala
200             205             210             215

Gln Met Leu Glu Val Met Phe Lys Gly Glu Ile Phe His Arg Asn His
            220             225             230

Arg Ser Pro Val Thr Leu Leu Ala Val Met Ser Leu Pro Glu Glu
            235             240             245

His Asn Lys Met Val Tyr Phe Ala Ile Ser Asp Tyr Val Phe Asn Thr
        250             255             260

Ala Ser Leu Val Tyr His Glu Glu Gly Tyr Leu Asn Phe Ser Ile Thr
265             270             275

Asp Glu Met Ile Pro Pro Asp Ser Asn Ile Arg Leu Thr Thr Lys Ser
280             285             290             295

Phe Arg Pro Phe Val Pro Arg Leu Ala Arg Leu Tyr Pro Asn Met Asn
            300             305             310

Leu Glu Leu Gln Gly Ser Val Pro Ser Ala Pro Leu Leu Asn Phe Ser
            315             320             325

Pro Gly Asn Leu Ser Val Asp Pro Tyr Met Glu Ile Asp Ala Phe Val
        330             335             340

Leu Leu Pro Ser Ser Ser Lys Glu Pro Val Phe Arg Leu Ser Val Ala
        345             350             355

Thr Asn Val Ser Ala Thr Leu Thr Phe Asn Thr Ser Lys Ile Thr Gly
360             365             370             375

Phe Leu Lys Pro Gly Lys Val Lys Val Glu Leu Lys Glu Ser Lys Val
```

```
                       380                 385                 390
Gly Leu Phe Asn Ala Glu Leu Glu Ala Leu Leu Asn Tyr Tyr Ile
                395                 400                 405
Leu Asn Thr Phe Tyr Pro Lys Phe Asn Asp Lys Leu Ala Glu Gly Phe
                410                 415                 420
Pro Leu Pro Leu Leu Lys Arg Val Gln Leu Tyr Asp Leu Gly Leu Gln
        425                 430                 435
Ile His Lys Asp Phe Leu Phe Leu Gly Ala Asn Val Gln Tyr Met Arg
440                 445                 450                 455
Val
```

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (D) OTHER INFORMATION: "LBP-10"

(xi) SEQUENCE DESCRIPTION: SEQ ID NO:7:

GAGATCGATA GTTTCGCCGA C                                       21

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (D) OTHER INFORMATION: "LBP-8"

(xi) SEQUENCE DESCRIPTION: SEQ ID NO:8:

CTGGCTAACC GTGGGACG                                          18

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (D) OTHER INFORMATION: "LBP-11"

(xi) SEQUENCE DESCRIPTION: SEQ ID NO:9:

ACTATCGATC TCTGTTGTAA                                      20

(2) INFORMATION FOR SEQ ID NO:10:

(i) SEQUENCE CHARACTERISTICS:
        (A) LENGTH: 29 base pairs
        (B) TYPE: nucleic acid (C) STRANDEDNESS: single
        (D) TOPOLOGY: linear (ii) MOLECULE TYPE: DNA (ix) FEATURE:
        (A) NAME/KEY: misc_feature
        (D) OTHER INFORMATION: "LBP-Bsm"

(xi) SEQUENCE DESCRIPTION: SEQ ID NO:10:

GAATGCAGCC AACCCCGGCT TGGTCGCCA                29

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (D) OTHER INFORMATION: "BPI-63"

(xi) SEQUENCE DESCRIPTION: SEQ ID NO:11:

AAAATCGATT CTGTGGCTGG                           20

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (D) OTHER INFORMATION: "BPI-7"

(xi) SEQUENCE DESCRIPTION: SEQ ID NO:12:

GAACTTGGTT GTCAGTCG                             18

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (D) OTHER INFORMATION: "BPI-64"

(xi) SEQUENCE DESCRIPTION: SEQ ID NO:13:

AGAATCGATT TTGGTCATTA                           20

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear -continued

```
    (ii) MOLECULE TYPE: DNA (ix) FEATURE:
         (A) NAME/KEY: misc_feature
         (D) OTHER INFORMATION: "BPI-40"

(xi) SEQUENCE DESCRIPTION: SEQ ID NO:14:

TGATCTGAAG CTGGGCAG                                                    18
```

METHOD FOR POTENTIATING BPI PROTEIN PRODUCT BACTERICIDAL ACTIVITY BY ADMINISTRATION OF LBP PROTEIN PRODUCTS

This is a Continuation of U.S. application Ser. No. 08/274,303, filed Jul. 11, 1994, now U.S. Pat. No. 5,770,561, which is a continuation-in-part of U.S. patent application Ser. No. 08/093,201 filed Jul. 14, 1993, now abandoned.

BACKGROUND OF THE INVENTION

The present invention relates generally to methods of treating gram-negative bacterial infections and the sequelae thereof and more specifically to the use of bactericidal/permeability-increasing protein (BPI) and BPI protein products in treatment of such infections.

BPI is a protein isolated from the granules of mammalian polymorphonuclear leukocytes (PMNs), which are blood cells essential in the defense against invading microorganisms.

Human BPI protein has been isolated from polymorphonuclear neutrophils by acid extraction combined with either ion exchange chromatography [Elsbach. *J. Biol. Chem.,* 254:11000 (1979)] or *E. coli* affinity chromatography [Weiss et al., *Blood,* 69:652 (1987)] referred to herein as natural BPI and has potent bactericidal activity against a broad spectrum of gram-negative bacteria. The molecular weight of human BPI is approximately 55,000 daltons (55 kD). The amino acid sequence of the entire human BPI protein, as well as the DNA encoding the protein, have been elucidated in FIG. 1 of Gray et al., *J. Biol. Chem.,* 264:9505 (1989), incorporated herein by reference.

The bactericidal effect of BPI has been shown to be highly specific to sensitive gram-negative species, while being non-toxic for other microorganisms and for eukaryotic cells. The precise mechanism by which BPI kills bacteria is as yet unknown, but it is known that BPI must first attach to the surface of susceptible gram-negative bacteria. This initial binding of BPI to the bacteria involves electrostatic and hydrophobic interactions between the basic BPI protein and the negatively charged sites on lipopolysaccharides (LPS). LPS has been referred to as "endotoxin" because of the potent inflammatory response that it stimulates. LPS induces the release of mediators by host inflammatory cells which may ultimately result in irreversible endotoxic shock. BPI binds to lipid A, the most toxic and most biologically active component of LPS.

In susceptible bacteria, BPI binding is thought to disrupt LPS structure, leading to activation of bacterial enzymes that degrade phospholipids and peptidoglycans, altering the permeability of the cell's outer membrane, and initiating events that ultimately lead to cell death. Elsbach and Weiss, *Inflammation: Basic Principles and Clinical Correlates,* eds. Gallin et al., Chapter 30, Review Press. Ltd. (1992). BPI is thought to act in two stages. The first is a sublethal stage that is characterized by immediate growth arrest, permeabilization of the outer membrane and selective activation of bacterial enzymes that hydrolyze phospholipids and peptidoglycan. Bacteria at this stage can be rescued by plating on serum albumin supplemented media. The second stage, defined by growth inhibition that cannot be reversed by serum albumin, occurs after prolonged exposure of the bacteria to BPI and is characterized by extensive physiologic and structural changes, including penetration of the cytoplasmic membrane.

BPI is also capable of neutralizing the endotoxic properties of LPS to which it binds. Because of its gram negative bactericidal properties and its ability to neutralize LPS, BPI can be utilized for the treatment of mammals suffering from diseases caused by Gram-negative bacteria, such as bacteremia or sepsis.

A proteolytic fragment corresponding to the N-terminal portion of human BPI holoprotein possesses substantially all the antibacterial efficacy of the naturally-derived 55 kD human holoprotein. In contrast to the N-terminal portion, the C-terminal region of the isolated human BPI protein displays only slightly detectable anti-bacterial activity. Ooi et al., *J. Exp. Med.,* 174:649 (1991). A BPI N-terminal fragment, which is the expression product of a gene encoding the first 199 amino acid residues of the human BPI holoprotein and comprising approximately the first 193 to 199 amino acid residues of human BPI hgoloprotein and referred to as "rBPI$_{23}$", has been produced by recombinant means as a 23 kD protein. Gazzano-Santoro et al., *Infect. Immun.* 60:4754–4761 (1992).

Lipopolysaccharide binding protein (LBP) is a 60 kD glycoprotein synthesized in the liver which shows significant structural homology with BPI. LBP is found in the serum of normal humans at levels of 5–10 μg/mL but can reach levels of 50–100 μg/mL in septic patients. Schumann et al., *Science,* 249:1429 (1990) disclose the amino acid sequences and encoding cDNA of both human and rabbit LBP. Like BPI. LBP has a binding site for lipid A and binds to the LPS from rough (R-) and smooth (S-) form bacteria. Unlike BPI. LBP does not possess significant bactericidal activity. BPI has been observed to neutralize and inhibit LPS-induced TNF production resulting from interaction of LBP with CD14 on monocytes and macrophages. Marra et al., *J. Immunol.* 148: 532 (1992), Weiss et al., *J. Clin. Invest.* 90: 1122 (1992). In contrast, LBP is observed to enhance LPS-induced TNF production. Wright et al., *Science,* 249:1131 (1990). Thus, in contrast to BPI, LBP has been recognized as an immunostimulatory molecule. See, e.g., Seilhamer, PCT International Application WO 93/06228 which discloses a variant form of LBP which it terms LBP-β.

Recently, it has been discovered that there exist biologically active protein derivatives of LBP which are characterized by the ability to bind to LPS but which lack CD14-mediated immunostimulatory properties of the LBP holoprotein. Specifically, co-owned and copending U.S. patent application Ser. No. 08/261,660 (Gazzano-Santoro et al., "Lipopolysaccharide Binding Protein Derivatives") filed Jun. 17, 1994, now U.S. Pat. No. 5,731,415, which is a continuation-in-part of U.S. patent application Ser. No. 08/079,510 filed Jun. 17, 1993, now abandoned, the disclosures of which are hereby incorporated by reference, discloses LBP protein derivatives and LBP derivative hybrid proteins which are capable of binding LPS and which lack CD14-mediated immunostimulatory activity. Preferred LBP protein derivatives have been produced by recombinant expression of genes encoding amino terminal amino acid residues, such as amino acid residues 1–197, and the resulting protein designated rLBP$_{25}$.

Of interest to the present application are the disclosures of references which relate to the potentiation of BPI bactericidal activity by 15 kD proteins derived from the granules of rabbit PMNs designated p15. Ooi et al. *J. Biol. Chem.,* 265:15956 (1990) disclose two related 15 kD proteins derived from rabbit PMN granules which have no bactericidal activity by themselves but which potentiate the first sublethal stage of BPI antibacterial activity but have an inhibitory effect on the second lethal stage of BPI antibacterial activity. Levy et al., *J. Biol. Chem.,* 268: 6058–6063

(1993) disclose the sequences of cDNAs encoding the two rabbit proteins and report that the protein with the stronger potentiating effect reduces the required dose of BPI for the early bacteriostatic effect by about 20-fold.

SUMMARY OF THE INVENTION

The present invention provides methods and compositions for treating gram negative bacterial infections and the sequelae thereof in a subject comprising administering a BPI protein product in combination with an LBP protein product. The invention is based on the finding that LBP protein products potentiate the bactericidal properties of BPI protein products by as much as almost ten thousand fold. The potentiation is seen in both the early reversible stage of BPI activity as well as in the late, irreversible stage of BPI activity. The result is unexpected because no similar potentiating molecules have been described that act at both the early and late stages of BPI killing, because unlike BPI, LBP does not possess significant bactericidal activity, and because an excess of LBP over BPI (as exists physiologically in serum) might be expected to competitively inhibit the bactericidal activity of BPI by virtue of its binding with LPS on a bacterial cell surface. This result is further unexpected as the effects of LBP holoproteins are generally viewed as being of a harmful nature as the LBP holoprotein has an immunostimulatory effect leading to an undesirable cytokine cascade.

According to the invention, LBP protein products can be coadministered with BPI protein products in amounts effective to potentiate the bactericidal properties of the BPI protein product. The invention utilizes any of the large variety of BPI proteins and protein derivatives known to the art including BPI protein fragments and hybrid BPI protein molecules. While any of the variety of LBP protein products known to the art are contemplated to be useful according to the teachings of the invention, those LBP protein derivatives which lack CD14 mediated immunostimulatory properties and particularly those lacking the ability to mediate LPS activity through the CD14 receptor are preferred for use. Such LBP protein products would include $rBPI_{25}$, LBP derivative hybrid proteins including LBP/BPI hybrid proteins and LBP-Ig fusion proteins which are characterized by the ability to bind LPS but which lack CD-14 immunostimulatory activity. Also contemplated are dimeric forms of $rLBP_{25}$ such as those obtained by fusion with human gamma heavy chain hinge and Fc regions, similar Fc fusions which lack $CH_2$ and dimers formed by incorporation of reactive cysteines or other such moieties at the carboxy terminus of $LBP_{25}$. It is contemplated that such forms may have properties comparable or superior to endogenous LBP.

The combination of BPI protein product and LBP protein product may be administered systemically or topically to a subject suffering from a gram-negative bacterial infection. Topical administration can be in the form of salves, ophthalmic drops, or eardrops. The BPI protein product and LBP protein product can also be administered systemically, such as orally, intravenously, by intramuscular or subcutaneous injection, or aerosolized for pulmonary administration. In addition, the compositions of the invention can be used in a variety of in vitro uses such as use as a bactericide to decontaminate fluids and surfaces and to sterilize surgical and other medical equipment and implantable devices.

Numerous additional aspects and advantages of the invention will become apparent to those skilled in the art upon consideration of the following detailed description of the invention which describes presently preferred embodiments thereof.

DETAILED DESCRIPTION

Figure 1:
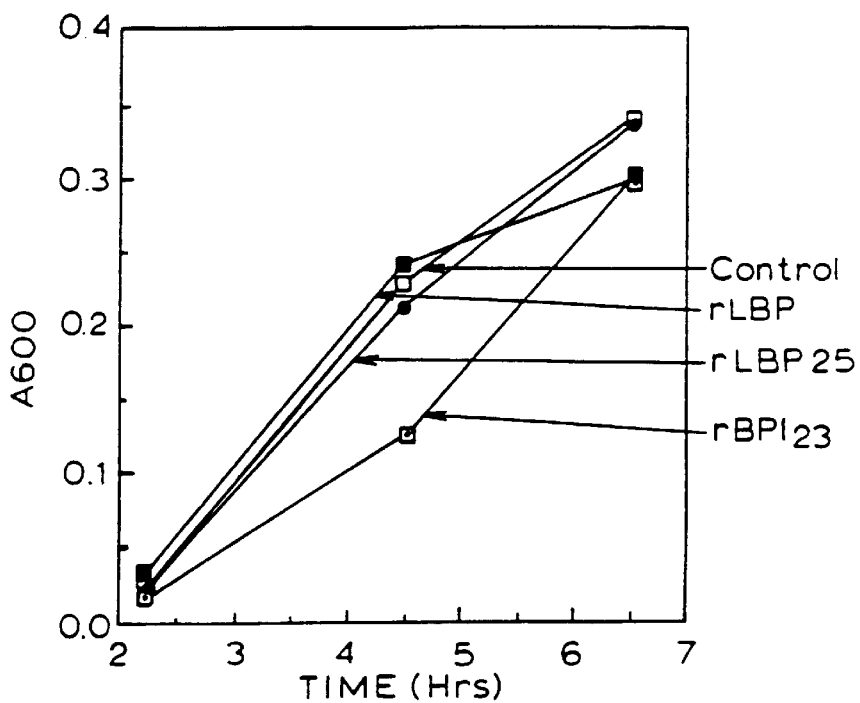
FIG. 1 depicts the results of a cell growth inhibition assay with rLBP, $rLBP_{25}$ and $rBPI_{23}$.

The present invention relates to methods of treating gram negative bacterial infections and the sequelae thereof in a subject comprising administering a BPI protein product and an LBP protein product. More specifically, the invention relates to the discovery that the co-administration of LBP protein products with BPI protein products potentiates activities including the gram-negative bactericidal activity of the BPI protein product. By "potentiate" is meant the ability to lower the effective concentration of BPI protein product that need be administered to achieve a particular effect such as a bactericidal effect. The LBP and BPI protein products may be coadministered or may be administered at various times one after another although it is generally preferred that the LBP protein product be administered prior to or simultaneously with the BPI protein product. The proteins may be administered systemically, such as intravenously. or by intramuscular or subcutaneous injection or may be administered topically. An advantage provided by the present invention is the ability to provide more effective systemic and topical treatment by virtue of the great potentiation of BPI anti-bacterial activity.

When practicing the methods of the invention, the LBP protein product is preferably an LBP protein derivative or LBP derivative hybrid protein which lacks CD14-mediated immunostimulatory properties according to co-owned and copending U.S. patent application Ser. No. 08/261.660 (Gazzano-Santoro et al., "Lipopolysaccharide Binding Protein Derivatives") filed Jun. 17, 1994, now U.S. Pat. No. 5,731,415, which is a continuation-in-part of U.S. patent application Ser. No. 08/079,510 filed Jun. 17, 1993 now abandoned, the disclosures of which are hereby incorporated by reference. Preferred LBP protein products which lack the CD-14-mediated immunostimulatory properties of the LBP holoprotein are amino-terminal LBP fragments such as those comprising the first 197 amino-terminal amino acids of the LBP holoprotein which is designated rLBP$_{25}$. Other suitable LBP protein products include LBP peptides which are able to bind to endotoxin and have the effect of potentiating bactericidal and other effects of BPI. Preferred LBP derivative hybrid proteins include LBP/BPI hybrid proteins and LBP-Ig fusion proteins which are characterized by the ability to bind LPS but which lack CD-14 immunostimulatory activity. Such LBP protein products are particularly preferred for use with the present invention because they do not exhibit the undesirable immunostimulatory properties of the LBP holoprotein.

The invention also provides improved methods of in vitro antisepsis for decontamination of fluids and surfaces comprising administering a BPI protein product in combination with an IBP protein product in an amount effective to potentiate the bactericidal properties of the BPI protein product. LBP protein products can be used to potentiate the bactericidal effects of BPI protein products in a variety of in vitro applications including sterilization of surgical and other medical equipment and implantable devices.

The invention further provides pharmaceutical compositions for treatment of gram-negative bacterial infection and the sequelae thereof comprising the combination of a BPI protein product and an LBP protein product which is present in an amount effective to potentiate the bactericidal properties of the BPI protein product. The pharmaceutical composition can comprise a pharmaceutically-acceptable diluent, adjuvant or carrier.

As another aspect of the invention, antiseptic bactericidal compositions are provided which comprise a BPI protein product and an LBP protein product in an amount effective to potentiate the bactericidal properties of the BPI protein product.

As used herein, "BPI protein product" includes naturally and recombinantly produced bactericidal/permeability-increasing protein; natural, synthetic, and recombinant biologically active polypeptide fragments of bactericidal/permeability increasing protein; and biologically active polypeptide analogs, including hybrid fusion proteins, of either bactericidal/permeability increasing protein or biologically active fragments thereof. The BPI protein products including biologically active fragments of BPI holoprotein which are to be administered according to the methods of this invention may be generated and/or isolated by any means known in the art. U.S. Pat. No. 5,198,541 the disclosure of which is hereby incorporated by reference discloses recombinant genes encoding and methods for expression of BPI proteins. Co-owned. copending U.S. patent application Ser. No. 07/885,501 filed May 19, 1992, now abandoned and a continuation-in-part thereof, U.S. patent application Ser. No. 08/072,063 filed May 19, 1993 now U.S. Pat. No. 5,439,807, which are hereby incorporated by reference, disclose novel methods for the purification of recombinant BPI protein products expressed in and secreted from genetically transformed mammalian host cells in culture and discloses how one may produce large quantities of recombinant BPI products suitable for incorporation into stable, homogeneous pharmaceutical preparations.

Biologically active fragments of BPI include biologically active molecules that contains the same amino acid sequence as a BPI holoprotein, except that the molecule lacks amino-terminal amino acids, internal amino acids, and/or carboxy-terminal amino acids of the holoprotein. By way of nonlimiting examples, such fragments include those described herein and a natural 25 kD fragment and a recombinant 23 kD amino-terminal fragment of the human BPI holoprotein referred to as rBPI$_{23}$. See, Gazzano-Santoro et al., *Infect. Immun.* 60:4754–4761 (1992). In that publication, an expression vector was used as a source of DNA encoding a recombinant expression product (rBPI$_{23}$) having the 31-residue signal sequence and encoding the first 199 amino acids of the N-terminus of the mature human BPI, as set out in SEQ ID NOS: 1 and 2 taken from Gray et al., supra, except that valine at position 151 is specified by GTG rather than GTC and residue 185 is glutamic acid (specified by GAG) rather than lysine (specified by AAG). Recombinant holoprotein having an approximate molecular weight of 50 kD and referred to herein as rBPI or as rBPI$_{50}$ has also been produced having the sequence set out in SEQ ID NOS: 1 and 2 taken from Gray et al., supra, with the exceptions noted for rBPI$_{23}$ and with the exception that residue 417 is alanine (specified by GCT) rather than valine (specified by GTT).

Biologically active analogs of BPI include but are not limited to recombinant hybrid fusion proteins comprising BPI holoprotein or biologically active fragment thereof, and at least a portion of at least one other polypeptide. Such proteins are described by Theofan et al. in co-owned, copending U.S. patent application Ser. No. 08/064,693 filed May 19, 1993, now U.S. Pat. No. 5,643,570, which is a continuation-in-part application of U.S. patent application Ser. No. 07/885.911. filed May 19, 1992, now abandoned, the disclosures of which are incorporated herein by reference in their entirety and include hybrid fusion proteins comprising, at the amino terminal end. a BPI protein or a biologically active fragment thereof and, at the carboxy terminal end, at least one constant domain of an immunoglobulin heavy chain or allelic variant thereof.

Biologically active analogs of BPI also include but are not limited to BPI protein products wherein one or more amino acid residue has been replaced by a different amino acid. For example, co-owned, copending U.S. patent application Ser. No. 08/013,801 (Theofan et al., "Stable Bactericidal/ Permeability-Increasing Protein Products and Pharmaceutical Compositions Containing the Same," filed Feb. 2, 1993) now U.S. Pat. No. 5,420,019, which is incorporated herein by reference, discloses polypeptide analogs of BPI and BPI fragments wherein a cysteine residue at position 132 or at position 135 is replaced by a different amino acid. A preferred BPI protein product described by this application is the expression product of DNA encoding from amino acid 1 to approximately 193 or 199 of the N-terminal amino acids of BPI holoprotein, but wherein the cysteine at residue 132 is substituted with alanine and is designated rBPI$_{21}$Δcys or rBPI$_{21}$. Alternative useful BPI protein products include those which are the expression products of DNA encoding from amino acid 1 to approximately 193 or 199 of the N-terminal amino acids of BPI halo protein but wherein the cysteine at residue 175 is substituted with alanine or wherein the serine at residue 18 is substituted with cysteine.

Other BPI protein products useful according to the methods of the invention are peptides based on or derived from BPI such as those described in co-owned and copending U.S. patent application Ser. No. 08/209,762 filed Mar. 11, 1994, now U.S. Pat. No. 5,733,872, which is a continuation-in-part U.S. patent application Ser. No. 08/183,222 filed Jan. 14, 1994 now abandoned, which is a continuation-in-part of U.S. patent application Ser. No. 08/093,202 filed Jul. 15, 1993 now abandoned as continuation-in-part of U.S. patent application Ser. No. 08/030,644 filed Mar. 12, 1993 now U.S. Pat. No. 5,348,942. The disclosures of these applications are hereby incorporated by reference. Other useful BPI protein products include peptides based on or derived from BPI which are described in co-owned and copending U.S. patent application Ser. No. 08/274,299 filed Jul. 11, 1994 now abandoned and U.S. patent application Ser. No. 08/273, 540 filed Jul. 11, 1994 now abandoned, the disclosures of which are hereby incorporated by reference.

Still further BPI protein products useful according to the method of the invention include recombinant dimeric forms of a BPI protein product produced according to the methods disclosed in co-owned and copending U.S. patent application Ser. No. 08/212,132 filed Mar. 11, 1994 now U.S. Pat. No. 5,447,913, the disclosure of which is hereby incorporated by reference. Preferred dimeric products include dimeric BPI protein products wherein the monomers are amino terminal BPI fragments having amino acid residues of from about 1 to 175 to about 1 to 199 amino of the amino terminal of BPI holoprotein.

The invention further provides novel pharmaceutical compositions comprising combinations of BPI protein products and an LBP protein product in an amount effective to potentiate the bactericidal properties of the BPI protein product together with pharmaceutically acceptable diluents, adjuvants, and carriers. The compositions are useful in methods for treating a gram-negative bacterial infection, including the sequelae thereof such as endotoxin related hypotension and shock, and one or more of conditions associated therewith including fever, metabolic acidosis, disseminated intravascular coagulation and related clotting disorders, anemia, thrombocytopenia, leukopenia, adult respiratory distress syndrome and related pulmonary disorders, renal failure and related renal disorders, hepatobiliary disease and related central nervous system disorders. Such methods comprise administering an LBP protein derivative or LBP derivative hybrid protein to a subject suffering from a gram-negative bacterial infection, including the sequelae thereof.

When employed for treatment of a gram-negative bacterial infection, including the sequelae thereof, the BPI protein products and LBP protein products are preferably each administered parenterally and most preferably intravenously in amounts broadly ranging from about 0.1 milligram and about 100 milligrams per kilogram of body weight of the treated subject with preferred treatments ranging from about 1 milligrams and 25 milligrams per kilogram of body weight.

The administration of BPI protein products is preferably accomplished with a pharmaceutical composition comprising a BPI protein product and a pharmaceutically acceptable diluent, adjuvant, or carrier. The BPI protein product composition may be administered without or in conjunction with known antibiotics, surfactants, or other chemotherapeutic agents. Suitable antibiotics for use in combination with BPI protein products are disclosed in co-owned and copending U.S. patent application Ser. No. 08/273,401 filed Jul. 11, 1994, now abandoned, which is a continuation-in-part of U.S. patent application Ser. No. 08/125,651 filed on Sep. 22, 1993, now abandoned, the disclosures of which are incorporated herein by reference.

A preferred pharmaceutical composition containing BPI protein products comprises BPI at a concentration of 1 mg/ml in citrate buffered saline (0.02 M citrate, 0.15 M NaCl, pH 5.0) comprising 0.1% by weight of poloxamer 188 (Pluronic F-68, BASF Wyandotte, Parsippany, N.J.) and 0.002% by weight of polysorbate 80 (Tween 80, ICI Arnericas Inc., Wilmington, Del.). A preferred pharmaceutical composition comprising 2 mg/mL rBPI$_{21}$Δcys contains 5 mM citrate, 150 mM NaCl, pH 5.0, 0.2% poloxamer 188 and 0.002% polysorbate 80. Such preferred combinations are described in co-owned, copending, U.S. patent application Ser. No. 08/251,576 giled May 31, 1994, now U.S. Pat. No. 5,932,544, which is a continuation-in-part of U.S. patent application Ser. No. 08/190,869 filed Feb. 2, 1994, now U.S. Pat. No. 5,488,034, which is a continuation in part of U.S. patent application Ser. No. 08/012,360 (McGregor et al., "Improved Pharmaceutical Composition" filed Feb. 2, 1993) now abandoned, the disclosures of which are incorporated herein by reference.

As used herein, "LBP protein product" includes naturally and recombinantly produced lipopolysaccharide binding protein; natural, synthetic, and recombinant biologically active polypeptide fragments and derivatives of lipopolysaccharide binding protein; and biologically active polypeptide analogs, including hybrid fusion proteins, of either LBP or biologically active fragments thereof. LBP protein products useful according to the methods of the present invention include LBP holoprotein which can be produced by expression of recombinant genes in transformed eucaryotic host cells such as described in co-owned and copending U.S. patent application Ser. Number 08/261,660 (Gazzano-Santoro et al., "Lipopolysaccharide Binding Protein Derivatives" filed Jun. 17, 1994, now U.S. Pat. No. 5,731,415, which is a continuation-in-part of U.S. patent application Ser. No. 08/079,510 filed Jun. 17, 1993, now abandoned the disclosures of which are hereby incorporated by reference and designated rLBP or rLBP$_{50}$. Also described in that application are LBP protein derivatives which lack CD14-mediated immunostimulatory properties and particularly the ability to mediate LPS activity through the CD14 receptor are preferred for use. Such LBP protein products are preferred for use according to the present invention because excessive CD14-mediated immunostimulation is generally considered undesirable, and is particularly so in subjects suffering from infection.

Preferred LBP protein derivatives are characterized as N-terminal fragments having a molecular weight of about 25 kD. Most preferred are LBP amino-terminal fragments characterized by the amino acid sequence of the first 197 amino acids of the amino-terminus of LBP, as set out in SEQ ID NOS:3 and 4 and designated rLBP$_{25}$. Nevertheless, it is contemplated that LBP protein derivatives considerably smaller than 25 kD and comprising substantially fewer than the first 197 amino acids of the amino-terminus of the holo-LBP molecule are suitable for use according to the invention provided they retain the ability to bind to LPS. Moreover, it is contemplated that LBP protein derivatives comprising greater than the first 197 amino acid residues of the holo-LBP molecule including amino acids on the carboxy-terminal side of first 197 amino acids of the rLBP as disclosed in SEQ ID NOS:5 and 6 will likewise prove useful according to the methods of the invention provided they lack an element that promotes CD14-mediated immunostimulatory activity. It is further contemplated that those of skill in the art are capable of making additions, deletions and substitutions of the amino acid residues of SEQ ID NOS:3–6 without loss of the desired biological activities of the molecules. Still further, LBP protein products may be obtained by deletion, substitution, addition or mutation, including mutation by site-directed mutagenesis of the DNA sequence encoding the LBP holoprotein, wherein the LBP protein product maintains LPS-binding activity and lacks CD14-mediated immunostimulatory activity. Specifically contemplated are LBP hybrid molecules and dimeric forms which may result in improved affinity of LBP for bacteria and/or increased stability in vivo. These include LBP/BPI hybrid proteins and LBP-Ig fusion proteins. Such hybrid proteins further include those using human gamma 1 or gamma 3 hinge regions to permit dimer formation. Other forms of dimer contemplated to have enhanced serum stability and binding affinity include fusions with Fc lacking the CH$_2$ domain, or hybrids using leucine or helix bundles.

The following detailed description relates to administration of BPI protein products in combination with LBP protein products in amounts effective to potentiate the bactericidal activity of the BPI protein products. More specifically, Example I relates to LBP potentiation of BPI bactericidal activity in a broth growth assay. Example 2 relates to LBP potentiation of BPI bactericidal activity in a plate assay. Example 3 relates to Actinomycin D permeability assays utilizing rBPI$_{23}$, rLBP and combinations thereof. Example 4 relates to cell growth inhibition assays relating to the effect of cell density on the potentiation effect. Example 5 relates to cell growth inhibition assays for rBPI$_{23}$, rLBP and combinations thereof in the presence of BSA. Example 6 relates to LBP potentiation of various BPI protein products in plate assays. Example 7 relates to LBP potentiation of BPI permeabilization activity with Actinomycin D. Example 8 relates to LBP potentiation of BPI activity in a bacterial protein synthesis assay. Example 9 relates to a plate growth bactericidal assay with rBPI$_{23}$ in combination with an LBP/BPI hybrid protein (LBP(1–197)/BPI(200–456)). Example 10 relates to a plate growth bactericidal assay examining the effect of order of addition of rBPI$_{23}$ and rLBP on potentiation of BPI bactericidal activity.

EXAMPLE 1

LBP Protein Product Potentiation of BPI Bactericidal Activity in a Broth Assay

The effect of exemplary LBP protein products rLBP$_{25}$ and rLBP alone and in combination with an exemplary BPI protein product rBPI$_{23}$ on *E. coli* J5 grown to late log phase in a triethanolamine buffered minimal salt medium [TEA: Weiss et al., *J. Clin. Invest.* 65:619 (1980)] was determined. *E. coli* J5 is a rough UDP-galactose 4 epimerase negative mutant of the smooth strain 0111-B4. Specifically, the cells were grown overnight in TYE broth [Gazzano-Santoro et al., *Infect. Immun.* 60: 4754 (1992)] and then subcultured as a 1/200 dilution in TEA medium. The bacteria were harvested at late-logarithmic phase, washed and resuspended in 0.9% NaCl at an absorption calculated to obtain approximately $5\times10^8$ cells/mL. Ten μL of cells (~$5\times10^6$ cells) were incubated at 37° C. for 45 minutes in 200 μL of a buffered salts solution (10% Hanks Balanced Salts Solution, 40 mM Tris-HCl, pH 7.5, 0.10% casamino acids pH 7.4) with the BPI or LBP protein products. Two mL of nutrient broth was added and growth was followed for 6 hours.

The results of addition of either rLBP$_{25}$ or rLBP at 50 μg/mL to rBPI$_{23}$ at 1 μg/mL or a control (buffer) are illustrated in FIG. 1 and show that neither of the LBP protein products had a growth inhibitory effect in comparison to the BPI protein product.

Figure 2:
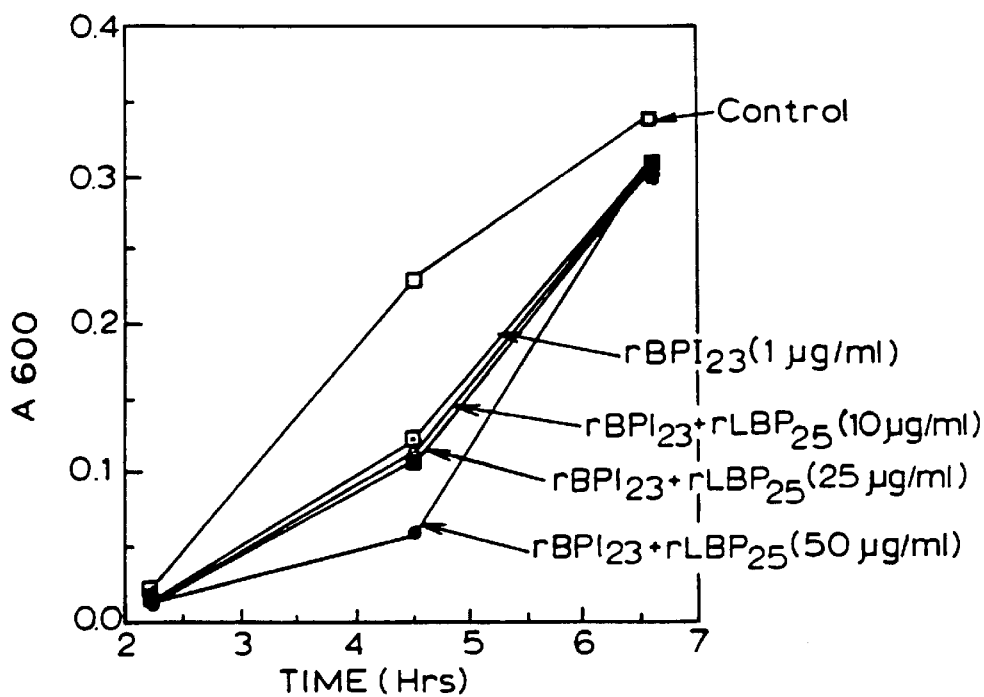
FIG. 2 depicts the results of a cell growth inhibition assay with $rBPI_{23}$ and combinations of $rBPI_{23}$ with various concentrations of $rLBP_{25}$.
Figure 3:
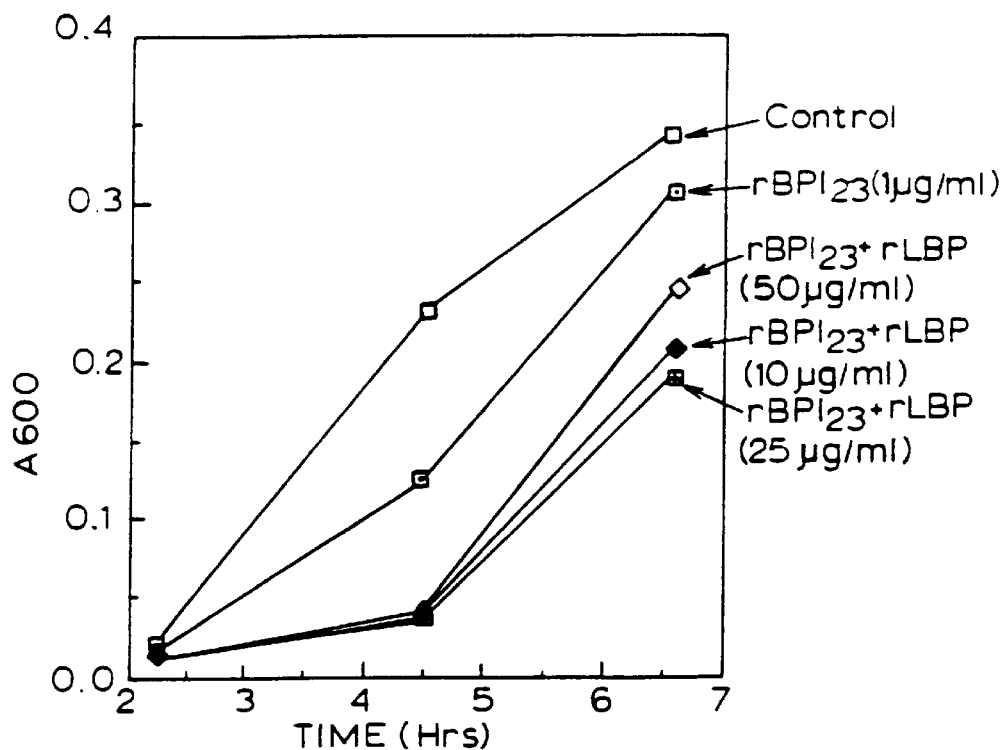
FIG. 3 depicts the results of a cell growth inhibition assay for $rBPI_{23}$ and combinations of $rBPI_{23}$ with various concentrations of rLBP.

Next, the effect of an LBP protein product on the activity of a BPI protein product was measured. Specifically, rBPI$_{23}$ was administered at a concentration of 1 μg/mL in combination with either rLBP$_{25}$ or rLBP at concentrations of 10, 25 or 50 μg/mL. The results illustrated in FIGS. 2 and 3 show that rLBP$_{25}$ slightly enhances the bactericidal activity of rBPI$_{23}$ (FIG. 2) and that rLBP (holoprotein) significantly potentiates the bactericidal activity of rBPI$_{23}$ (FIG. 3).

The effect of rLBP at a concentration of 10 μg/mL was then determined at various BPI protein concentrations according to the general methods above but wherein growth was followed at $A_{600}$. According to a first experiment. rBPI$_{23}$ was administered at concentrations from 2 μg/mL to 0.1 μg/mL with and without rLBP at a concentration of 10 μg/mL. In the second experiment. rBPI$_{23}$ was administered at concentrations of from 0.5 μg/mL to 0.01 μg/mL with and without rLBP at a concentration of 10 μg/mL.

Figure 4:
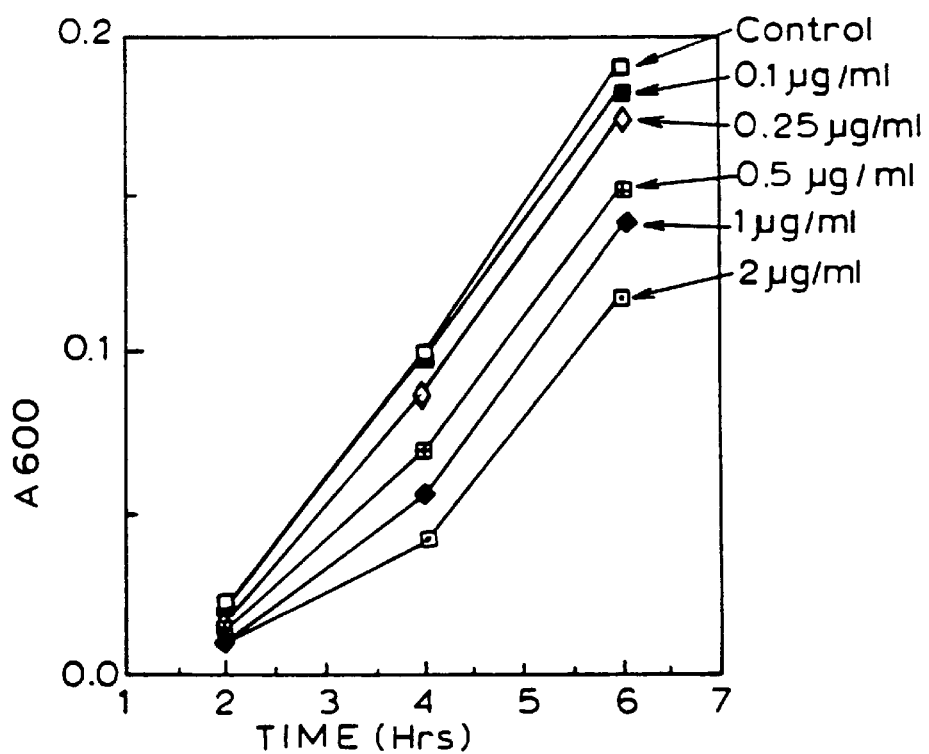
FIG. 4 depicts the results of a cell growth inhibition assay with $rBPI_{23}$ at various concentrations.
Figure 5:
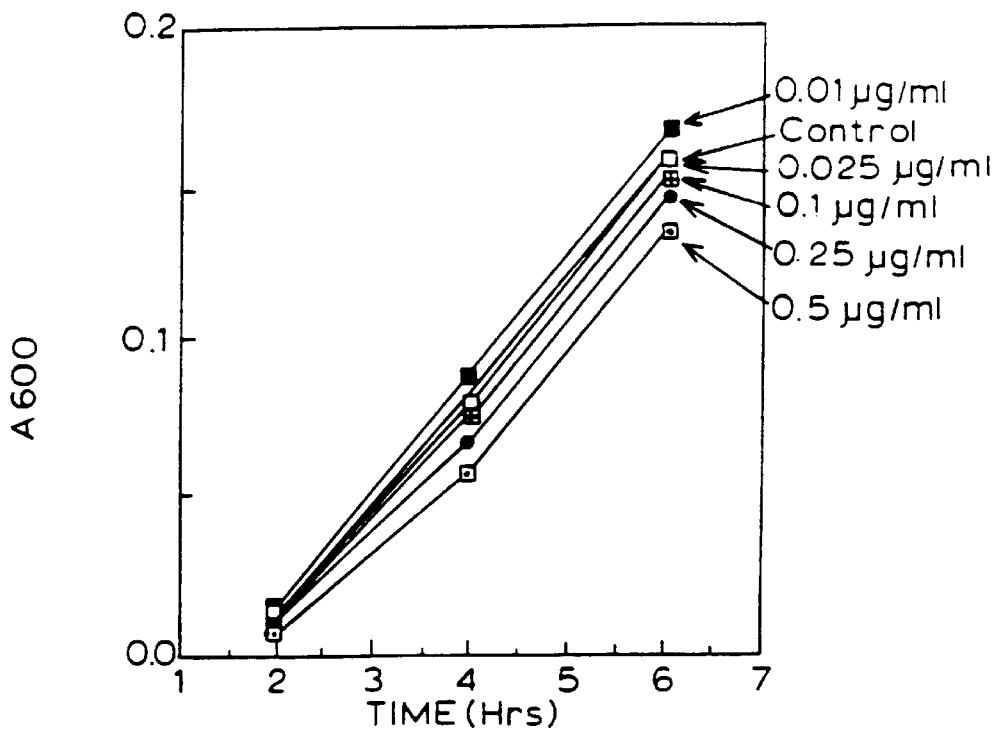
FIG. 5 depicts the results of a cell growth inhibition assay with $rBPI_{23}$ at various concentrations.
Figure 6:
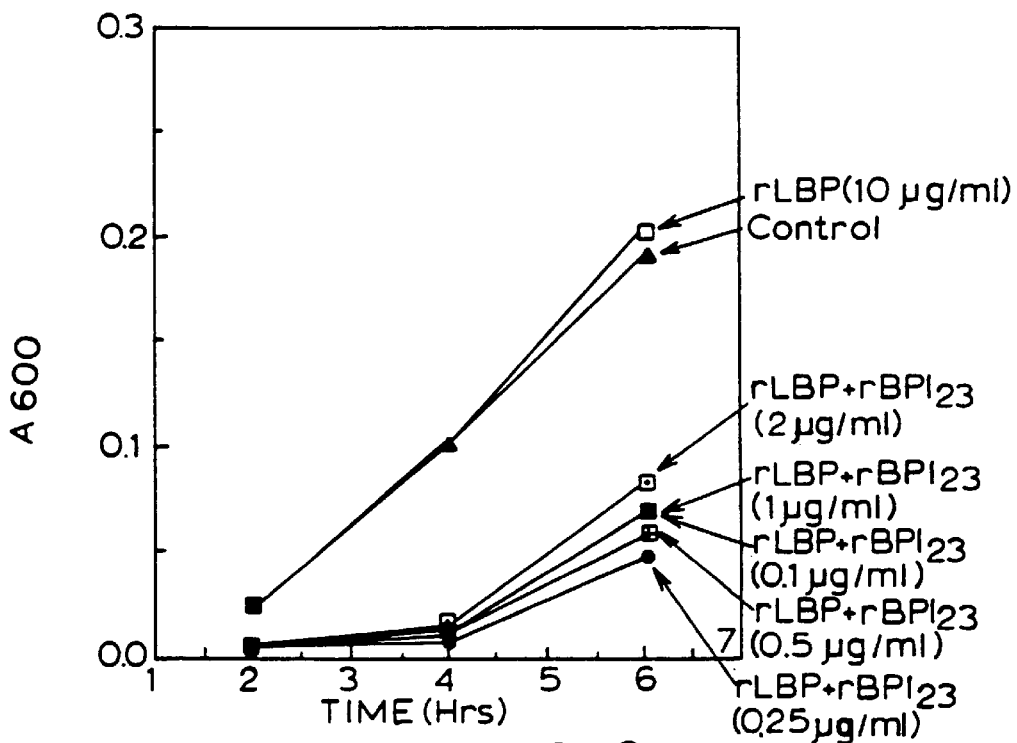
FIG. 6 depicts the results of a cell growth inhibition assay with rLBP and combinations of rLBP with various concentrations of $rBPI_{23}$.
Figure 7:
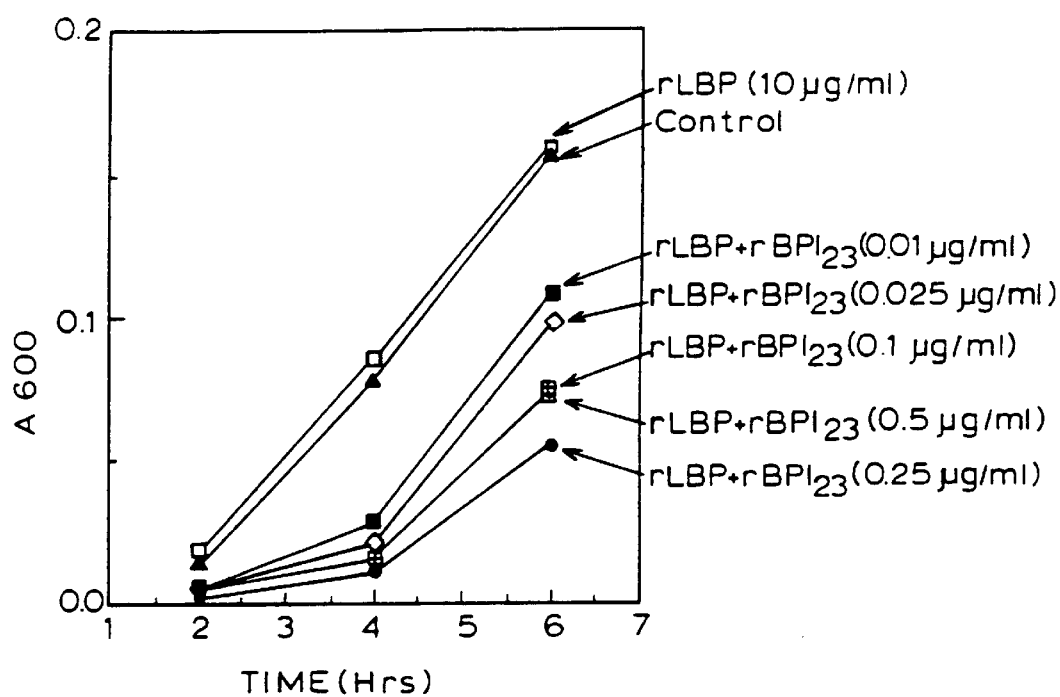
FIG. 7 depicts the results of a cell growth inhibition assay with LBP and combinations of rLBP and various concentrations of $rBPI_{23}$.

The results of administration of BPI protein alone illustrated in FIGS. 4 and 5 show that rBPI$_{23}$ alone has a measurable bactericidal effect only at concentrations at or above 0.5 μg/mL. The results illustrated in FIGS. 6 and 7 show a dramatic potentiation in the bactericidal activity of the BPI protein by coadministration of an LBP protein at 10 μg/mL. In both experiments, the maximal growth inhibitory effect was seen with administration of rLBP at 10 μg/mL with BPI$_{23}$ at a concentration of 0.25 μg/mL. The administration of rLBP alone had no inhibitory effect.

EXAMPLE 2

Potentiation as Determined in Plate Assays

The effect of exemplary LBP protein products on *E. coli* alone and in combination with an exemplary BPI protein product was studied in a plate growth assay to determine if the potentiation of BPI bactericidal activity by LBP results in a reduction of colony forming units. Specifically, *E. coli* J5 was grown to late log phase in TEA broth. Approximately $5 \times 10^6$ cells were incubated at 37° C. for 45 minutes in 200 µL of buffered salts solution (pH 7.4) with the $rBPI_{23}$ at concentrations of from 2.5 µg/mL to 0.001 µg/mL and/or with rLBP at 10 and 1 µg/mL. The samples were diluted in physiological saline and plated on nutrient agar.

Figure 8A:
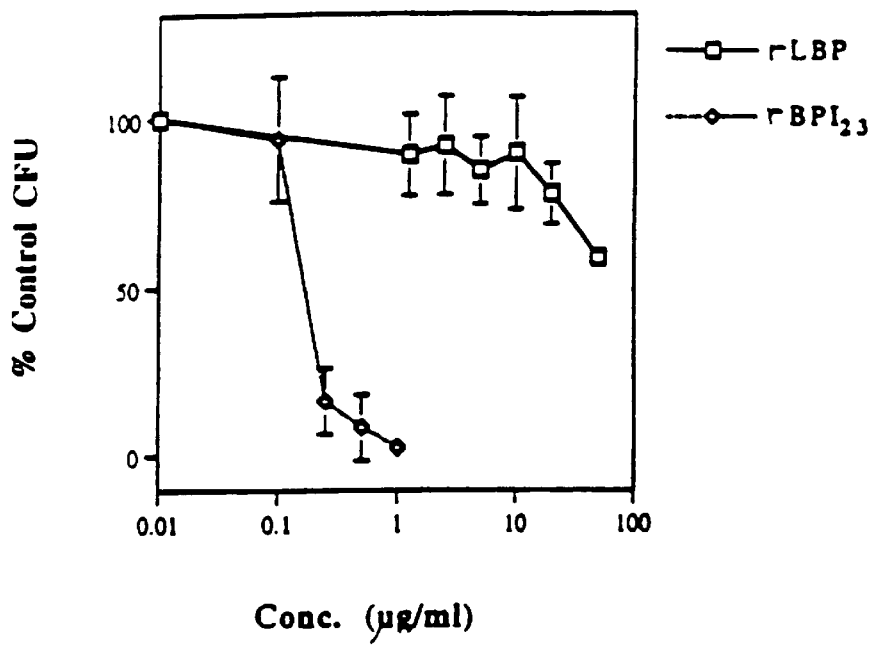
FIGS. 8a and 8b depict the results of a plate growth bactericidal assay with $rBPI_{23}$ and rLBP and combinations thereof.
Figure 8B:
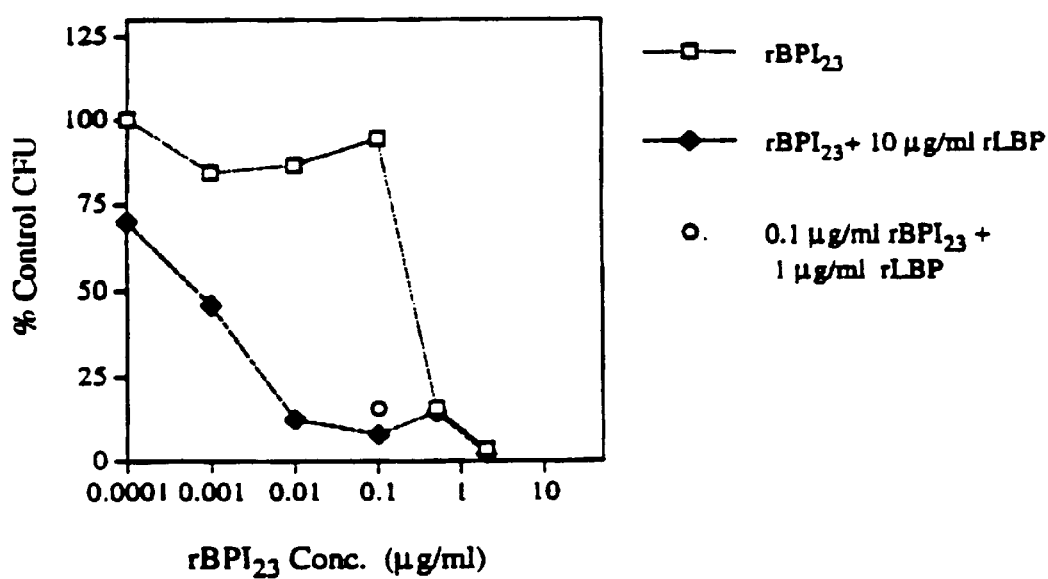

The results shown in FIG. 8a [wherein $rBPI_{23}$ is depicted by (—◇—) and rLBP is depicted by (—□—)] show that incubation of cells with $rBPI_{23}$ at about 1 µg/mL caused a 95% reduction in viable cell count but that incubation with $rBPI_{23}$ at or below 0.1 µg/mL failed to significantly reduce CFU relative to the negative control. Incubation with rLBP alone had no significant effect on the viable cell count at concentrations up to 10 µg/mL, but resulted in approximately 25% and 40% reductions in CFU at 20 and 50 µg/mL concentrations respectively. The results illustrated in FIG. 8b show that rLBP at 1 µg/mL (—○—) and 10 µg/mL (◆) potentiates the bactericidal activity of $rBPI_{23}$ compared to $rBPI_{23}$ alone (—□—).

Figure 9:
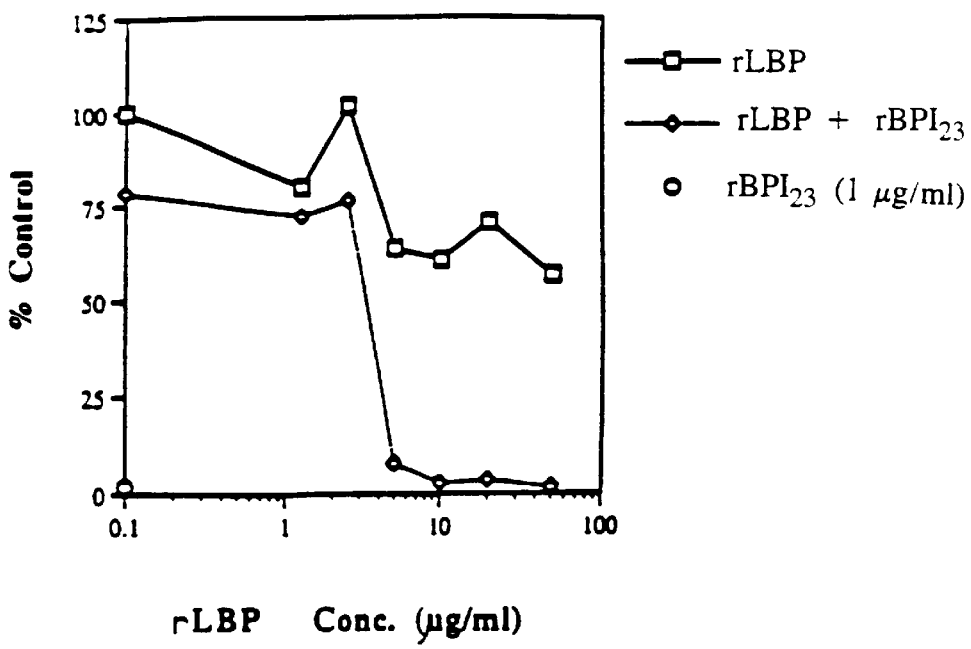
FIG. 9 depicts the results of a plate growth bactericidal assay with rLBP or $rBPI_{23}$ and the combination of rLBP with $rBPI_{23}$.
Figure 10:
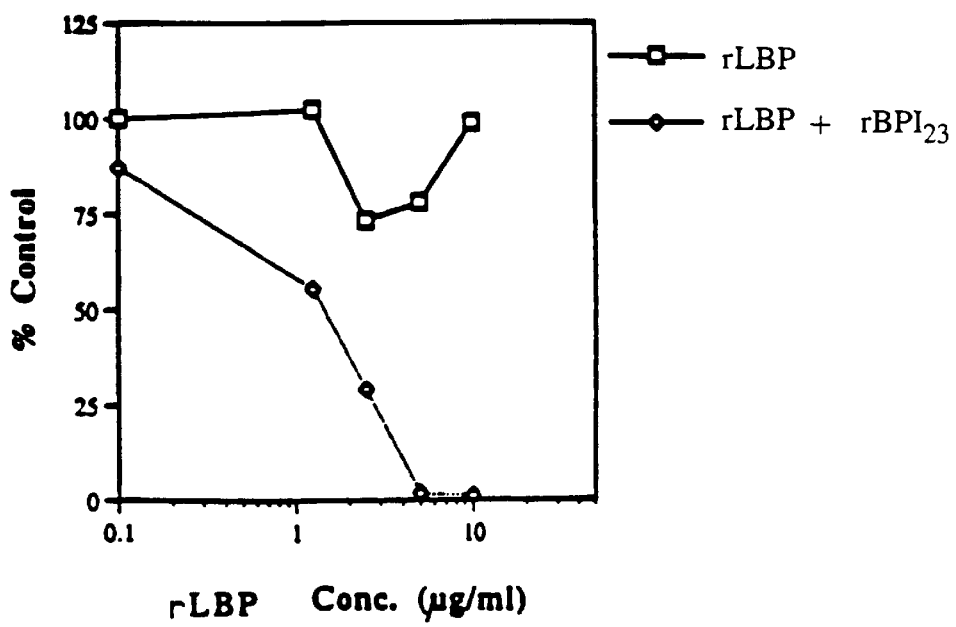
FIG. 10 depicts the results of a plate growth bactericidal assay with rLBP and the combination of rLBP with $rBPI_{23}$.
Figure 11:
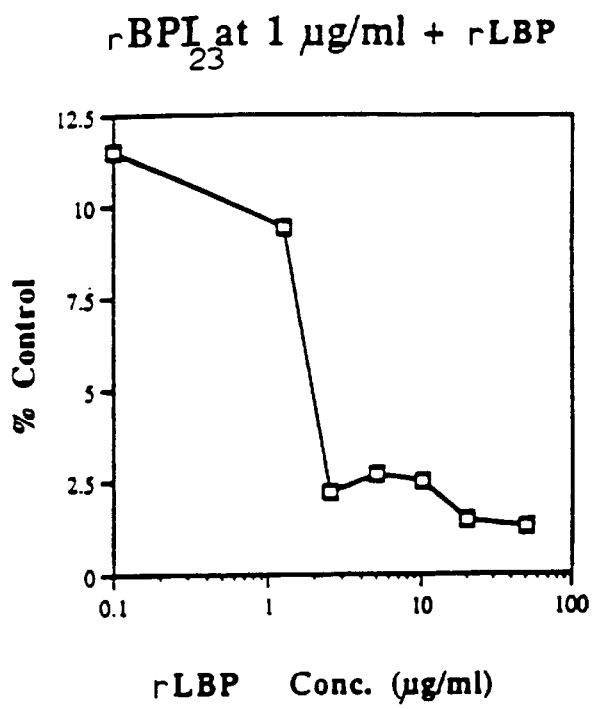
FIG. 11 depicts the results of a plate growth bactericidal assay with the combination of $rBPI_{23}$ with various concentrations of rLBP.

Additional plate assays were conducted to determine the effect of LBP protein product potentiation of BPI protein product bactericidal activity at various concentrations of both protein products. Specifically, approximately $4 \times 10^7$ cells/mL of *E. coli* J5 were incubated at 37° C. for about 45 minutes in 200 µL of buffered salts solution (pH 7.4) containing LBP at concentrations from 1 to 50 µg/mL and/or $rBPI_{23}$ at concentrations of 0.01, 0.1 and 1.0 µg/mL. The samples were diluted in physiological saline and plated on nutrient agar. The results of these experiments shown in FIGS. 9, 10 and 11 below indicate that rLBP alone has relatively little bactericidal activity but that it significantly enhances the bactericidal activity of $rBPI_{23}$, and particularly so at the lower BPI protein concentrations (0.1 and 0.01 µg/mL). In FIG. 9 rLBP the data is depicted as follows: rLBP, —□—; rLBP and $rBPI_{23}$ at 0.01 µg/mL, —◇—; and $rBPI_{23}$ alone at 1 µg/mL —○—. In FIG. 10 the data are depicted as follows: rLBP, —□—; rLBP with $rBPI_{23}$ at 0.1 µg/mL, —◇—. In FIG. 11 the data are depicted as follows: rLBP with $rBPI_{23}$ at 1 µg/mL, —□—. These results indicated that the optimal effect was obtained with 5–10 µg/mL rLBP depending upon the concentration of $rBPI_{23}$.

Figure 12:
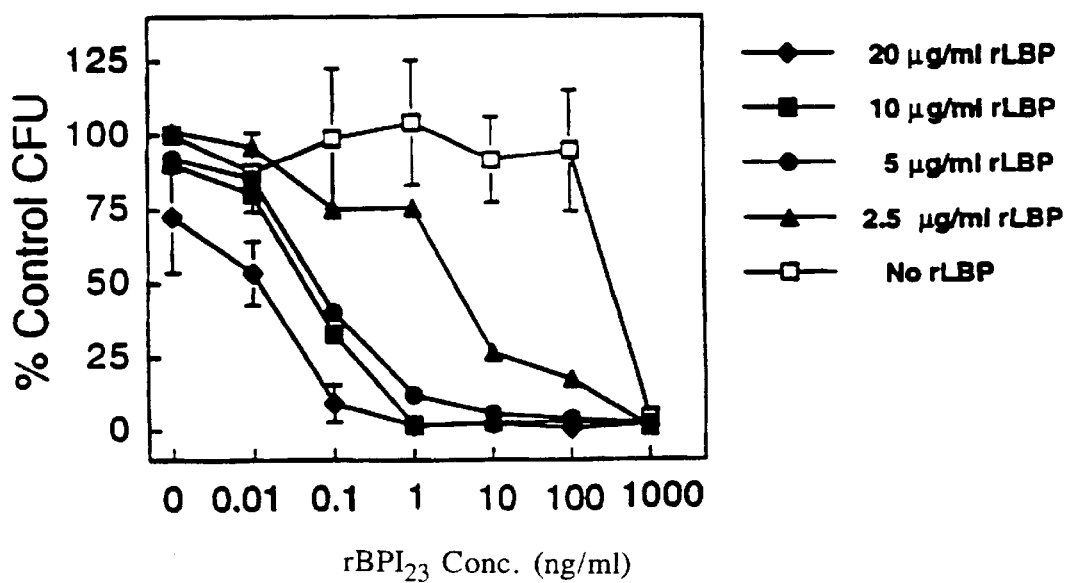
FIG. 12 depicts the results of a plate growth bactericidal assay with combinations of rLBP with $rBPI_{23}$ at various concentrations of $rBPI_{23}$ and rLBP.

Additional plate assays were conducted to further define the extent of LBP protein product potentiation of BPI protein products. Specifically, approximately $4 \times 10^7$ cells/mL of *E. coli* J5 were incubated at 37° C. for about 45 minutes in 200 µL of buffered salts solution (pH 7.4). The cells were then incubated with varying concentrations of $rBPI_{23}$ (1, 0.1, 0.01, 0.001, 0.0001 and 0.00001 µg/mL) and with various concentrations of rLBP (0, 1.25, 2.5, 5, 10, 20 and 50 µg/mL) for 45 minutes at 37° C., diluted in physiological saline and plated on nutrient agar. Selected results are shown in FIG. 12 with the data depicted as follows: $rBPI_{23}$ with no rLBP, —□—; $rBPI_{23}$ with 2.5 µg/mL rLBP. —▲—; $rBPI_{23}$ with 5 µg/mL rLBP, —●—; $rBPI_{23}$ with 10 µg/mL rLBP. —■—; and $rBPI_{23}$ with 20 µg/mL LBP, —◆—. The results suggest that the same extent of killing (~90–95%) is observed with 20 µg/mL rLBP with 0.1 ng/mL $BPI_{23}$ as with $rBPI_{23}$ at 1.0 µg/mL. This represents an approximate 10,000 fold potentiation of the bactericidal effects of BPI and suggests that a BPI/target cell ratio of only about 60 BPI molecules per cell is required to kill 90% of the cells.

Table 1 below shows the concentrations of $rBPI_{23}$ required to kill >95% of $4 \times 10^7$ *E. coli* J5 cells/mL in the presence of various concentrations of rLBP. The ratios were obtained by dividing the number of rLBP or $rBPI_{223}$ molecules per mL by $4 \times 10^7$. Only ~90% reduction in CFUs was achieved for the combination of 20 µg/mL rLBP with 0.1 ng/mL $rBPI_{23}$.

TABLE 1

| rLBP conc. (µg/mL) | rLBP conc. (Molecules/cell) | $rBPI_{23}$ conc. (ng/mL) | $rBPI_{23}$ conc. (Molecules/cell) |
| --- | --- | --- | --- |
| 0 | 0 | 1000 | ~600,000 |
| 5 | ~1,200,000 | 10 | ~6,000 |
| 10 | ~2,400,000 | 1 | ~600 |
| 20 | ~4,800,000 | 0.1 | ~60 |

Figure 13:
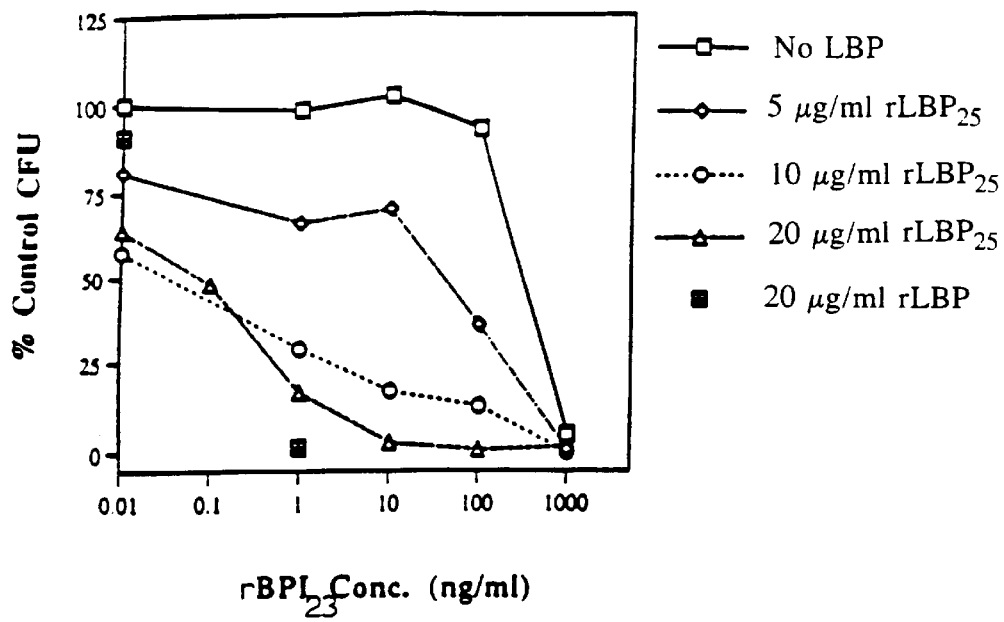
FIG. 13 depicts the results of a plate growth bactericidal assay with combinations of $rLBP_{25}$ with $rBPI_{23}$ at various concentrations of $rBPI_{23}$ and rLBP.

The experiment was then repeated substituting varying concentrations of $rLBP_{25}$ for rLBP with the results shown in FIG. 13. In that figure the data are depicted as follows: $rBPI_{23}$ with no rLBP, —□—; $rBPI_{23}$ with 5 µg/mL $rLBP_{25}$, —◇—; $rBPI_{23}$ with 10 µg/mL $rLBP_{25}$, —○—; $rBPI_{23}$ with 20 µg/mL $rLBP_{25}$, —△—; and $rBPI_{23}$ with 20 µg/mL LBP (a square containing a cross). The results shown in FIG. 13 indicate that $rLBP_{25}$ potentiates the bactericidal activity of $rBPI_{23}$ but that it is slightly less effective than rLBP at doing so.

Figure 14:
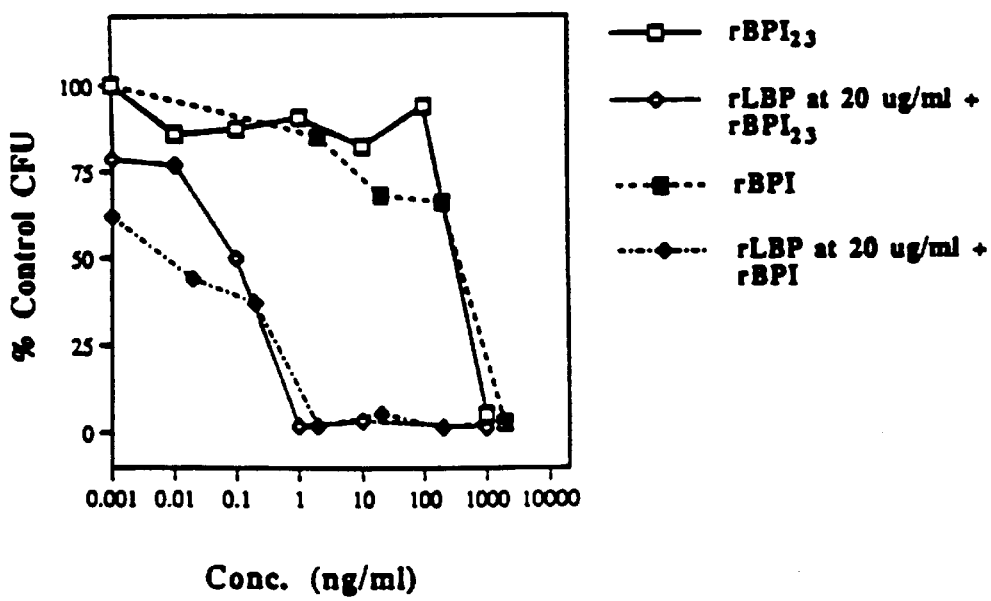
FIG. 14 depicts the results of a plate growth bactericidal assay with $rBPI_{23}$, rBPI and combinations of rLBP with various concentrations of $rBPI_{23}$ or rBPI.

The experiment was then further repeated utilizing rBPI with the results shown in FIG. 14. In that figure the d ata depicted as follows: $rBPI_{23}$ alone, —□—; $rBPI_{23}$ with 20 µg/mL rLBP, —◇—; rBPI alone (a square containing a cross) and rBPI with 20 µg/mL rBPI, —◆—. The results illustrated in FIG. 14 show that rLBP at 20 µg/mL also potentiated the activity of full-length recombinant BPI in a manner similar to that of $rBPI_{23}$.

EXAMPLE 3

Figure 15A:
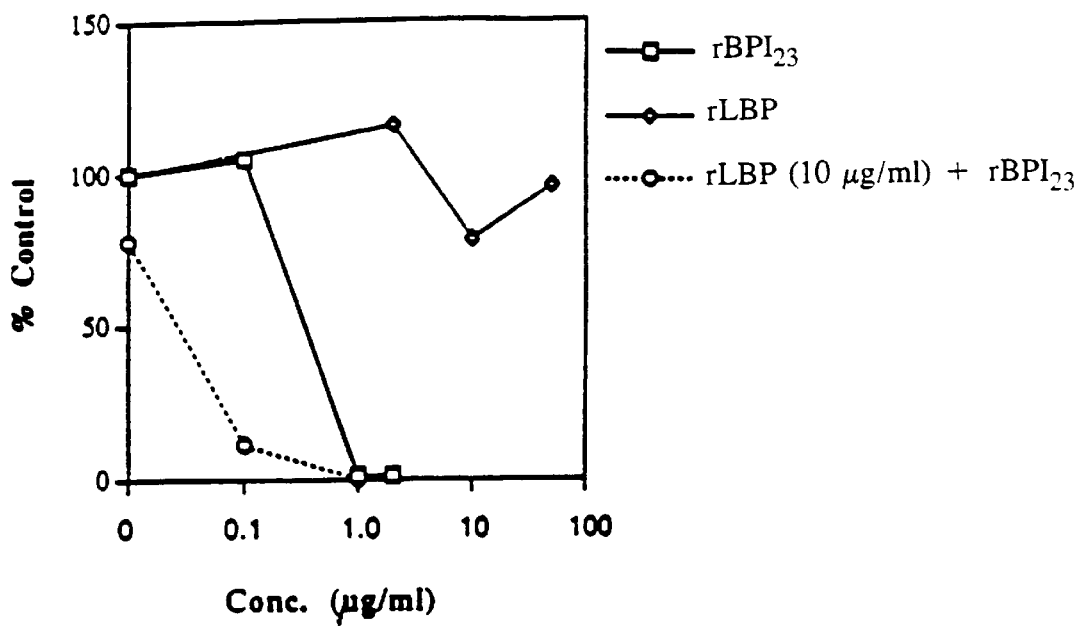
FIGS. 15a, 15b and 15c depict the results of Actinomycin D permeability assays utilizing $rBPI_{23}$, rLBP and combinations thereof.
Figure 15B:
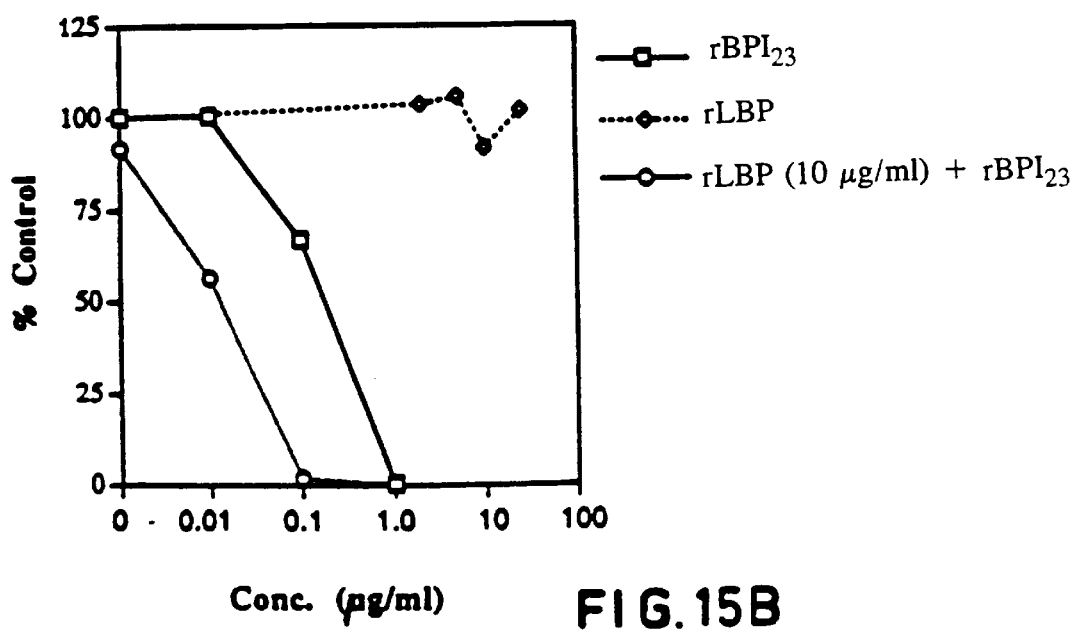
Figure 15C:
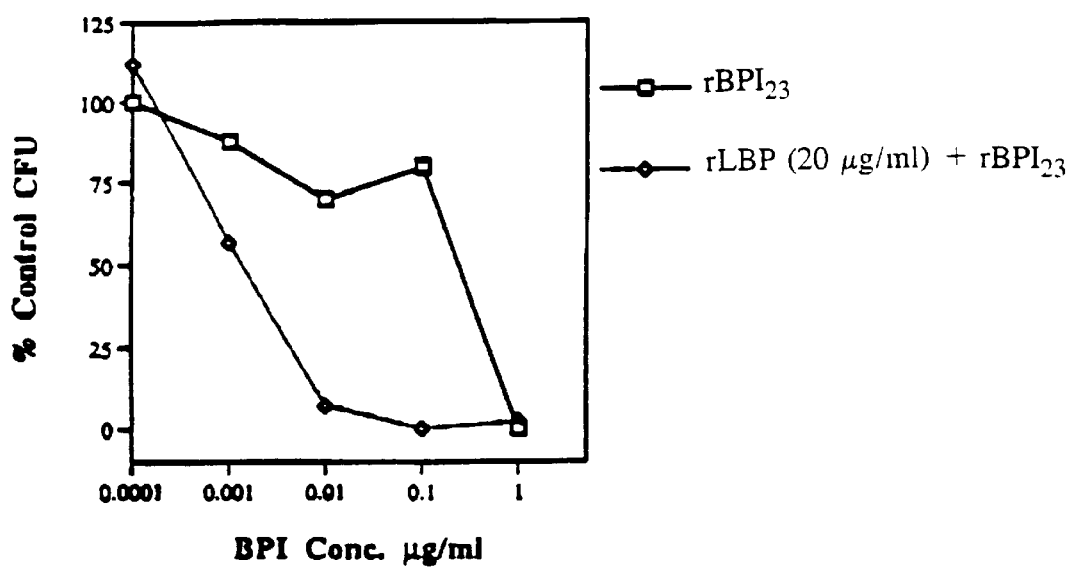

LBP Potentiation of BPI Permeabilization Activity with Actinomycyn D in a Plate Assay The effect of LBP protein products on the permeability increasing properties of BPI protein products were determined in a plate assay. Specifically, approximately $4 \times 10^7$ cells/mL of *E. coli* J5 were incubated at 37° C. for 10 minutes in 200 µL of buffered salts solution (pH 7.4) containing actinomycin D at 50 µg/mL and either rLBP at concentrations from 1 to 50 µg/mL or $rBPI_{23}$ at concentrations of from 0.01 to 2 µg/mL with or without rLBP at a concentration of 10 µg/mL and $rBPI_{23}$ at 0.001 to 1 µg/mL with rLBP at 20 µg/mL. The resulting samples were diluted in physiological saline and plated on nutrient agar supplemented with 0.1% BSA. The results of the two experiments which were performed with rLBP at 10 µg/mL and various concentrations of $rBPI_{23}$ are shown in FIGS. 15a and 15b. In FIGS. 15a and 15b the data are depicted as follows: $rBPI_{23}$ alone —□—; rLBP alone —◇—; and $rBPI_{23}$ in combination with rLBP at 10 µg/mL, —○—. The results suggest that while rLBP has little or no permeabilizing activity by itself it is able to significantly enhance t he permeabilizing activity of $rBPI_{23}$. Results of an experiment performed with rLBP at 20 µg/mL and $rBPI_{23}$ at various concentrations suggest that rLBP potentiates BPI at up to 100 fold as illustrated in FIG. 15c. In FIG. 15c, $rBPI_{23}$ alone is represented by (—□—), and $rBPI_{23}$ with 20µg/mL rLBP is represented by (—◇—).

EXAMPLE 4

Figure 16:
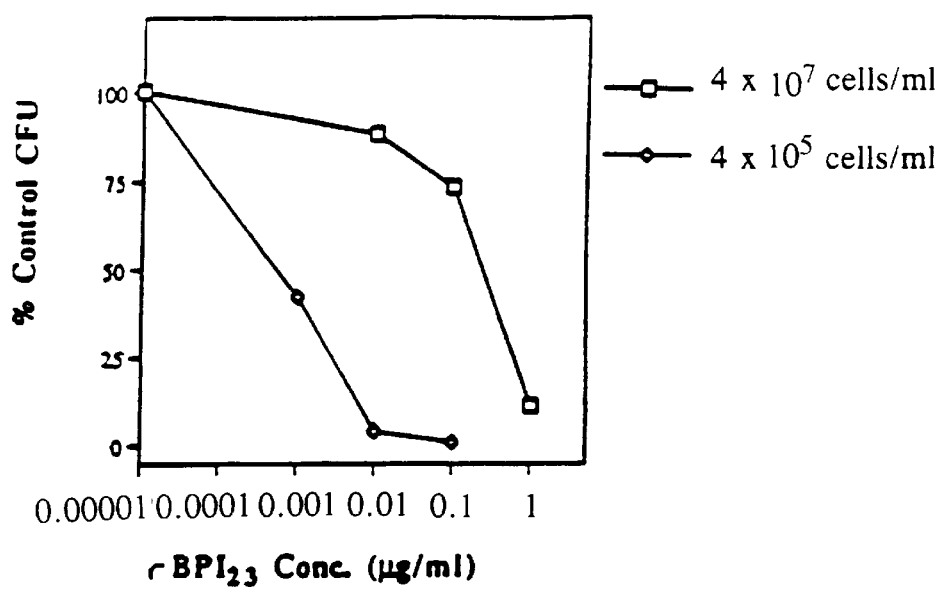
FIG. 16 depicts the results of a plate growth bactericidal assay with $rBPI_{23}$ using different cell densities.
Figure 17:
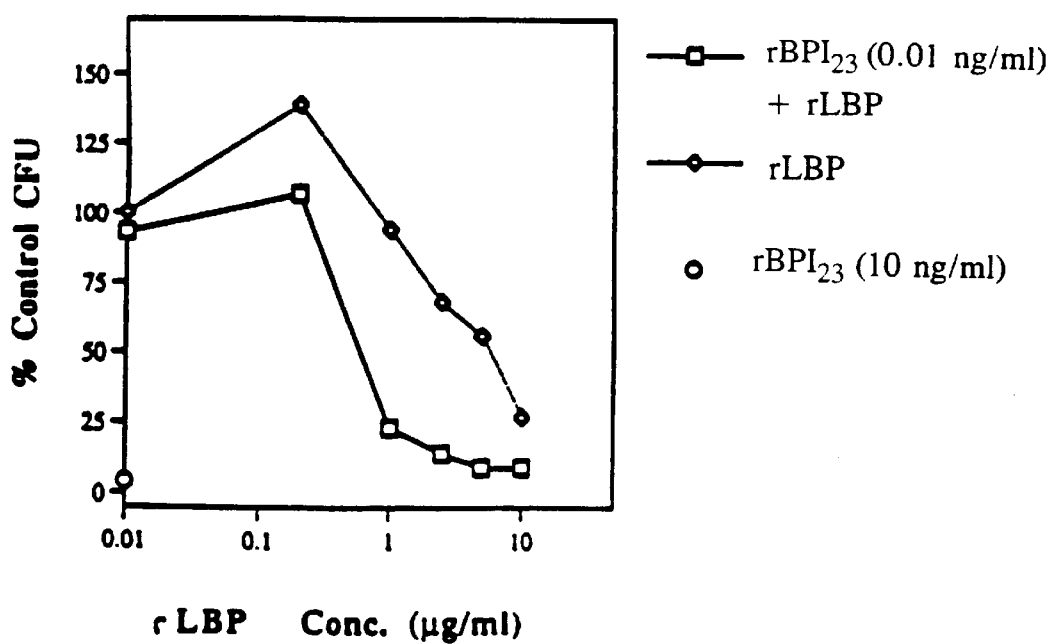
FIG. 17 depicts the results of a plate growth bactericidal assay with rLBP, $rBPI_{23}$ and combinations thereof using different cell densities.

Effects of Cell Density on LBP Potentiation of BPI Bactericidal Activity in a Plate Assay The effect of *E. coli* cell density on the potentiation effect was examined. Specifically, the concentration of rBPI required to kill approximately 90% of the cells ($IC_{90}$) was examined at $4 \times 10^7$ cells/mL versus $4 \times 10^5$ cells/mL and compared to the concentration of $rBPI_{23}$ needed to achieve the same degree of killing in the presence of rLBP at these cell densities. The results are shown in FIGS. 16 and 17. In FIG. 16 $4 \times 10^7$ cells/mL are represented by (—□—) and the $4 \times 10^5$ cells/mL are represented by (—◇—). In FIG. 17 the data are depicted as follows: rLBP with 0.01 ng/mL $rBPI_{23}$—□—; rLBP alone —◇—; and $rBPI_{23}$ at 10 ng/mL, ○.

The results illustrated in FIGS. 16 and 17 show that when the *E. coli* concentration is reduced by 100-fold, i.e. from $4 \times 10^7$ cells/mL to 4×10G5G cells/mL, the concentration of BPI protein needed to achieve an $IC_{90}$ is also reduced by about 100-fold (i.e. from 1 μg/mL to 10 ng/mL $rBPI_{23}$ results in an $IC_{90}$). By comparison, at $4 \times 10^5$ cells/mL, an rLBP concentration of from 2.5 to 5 μg/mL in combination with 0.01 ng/mL of $rBPI_{23}$ (a concentration which is 1000-fold less than needed for $rBPI_{23}$ to achieve an $IC_{90}$ at this cell density) is needed to achieve an $IC_{90}$. Thus, at the lower cell density, the BPI killing effect is BPI/target ratio dependent while the LBP potentiation is more dependent on maintaining the concentration of LBP within a physiologically-relevant range.

EXAMPLE 5

Effect Of BSA on LBP Potentiation of BPI Bactericidal Activity in a Plate Assay

Figure 18A:
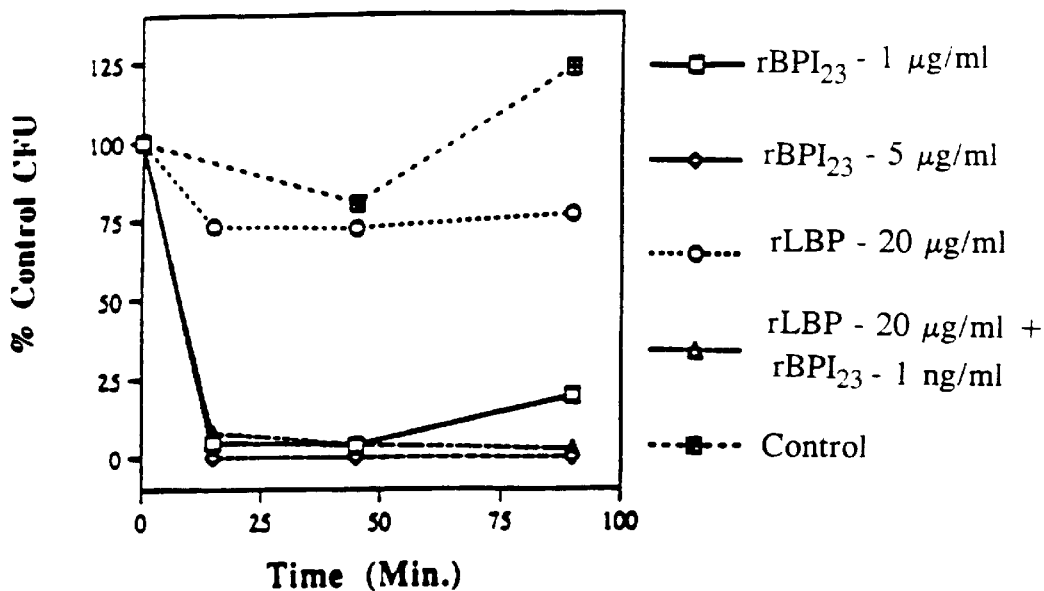
FIGS. 18a and 18b depict the results of plate growth bactericidal assays with rLBP, $rBPI_{23}$ and combinations thereof in the presence and absence of BSA.
Figure 18B:
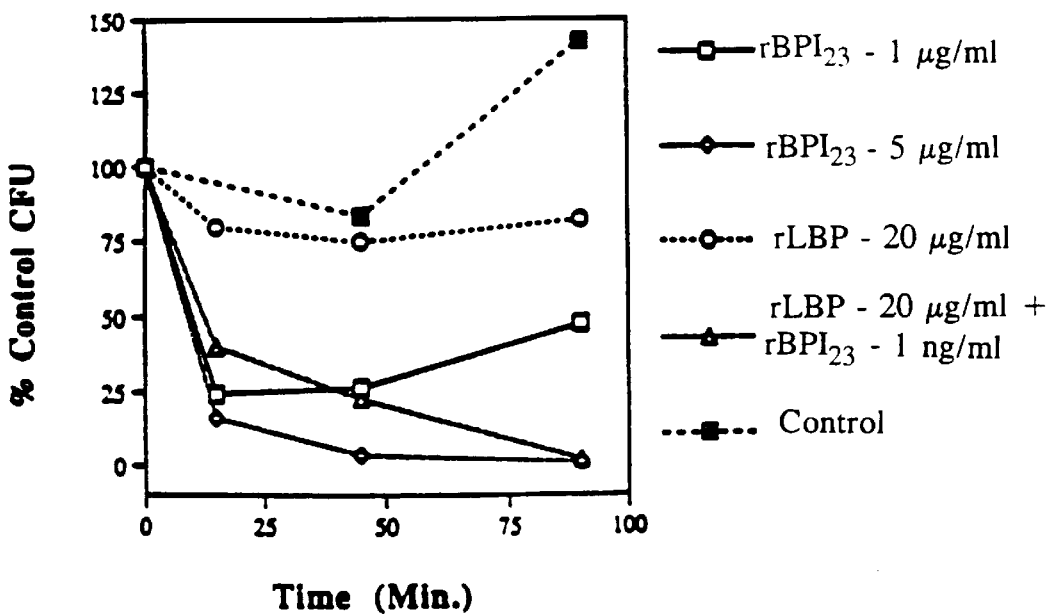

In this example the effect of BSA on potentiation by LBP of the bactericidal effect of $rBPI_{23}$ protein was determined in a plate assay. It is noted that experiments reported by Ooi et al., *J. Biol. Chem.*, 265:15956 (1990) showed that potentiation of BPI by p15 did not occur when cells were plated on BSA supplemented nutrient agar. According to this example, *E. coli* J5 cells at a concentration of $4 \times 10^7$ cells/mL in 200 μl of buffered salts solution were incubated with $rBPI_{23}$ at concentrations of 1 and 5 μg/mL and with rLBP at 20 μg/mL with and without $rBPI_{23}$ at 1 ng/mL for 15, 45 and 90 minutes at 37° C. diluted in physiological saline and were plated onto agar plates supplemented with 0.1% BSA or unsupplemented control plates. The results are shown in FIGS. 18a and 18b. In FIGS. 18a and 18b with the data depicted as follows: $rBPI_{23}$ at 1 μg/mL, —□—; $rBPI_{23}$ at 5 μg/mL, —◇—; rLBP at 20 μg/mL, —○—; 20 μg/mL rLBP with 1 ng/mL $rBPI_{23}$, —Δ— and the squares containing the crosses represent controls.

The results in FIGS. 18a (control: without BSA) or 18b (with BSA) show that BPI protein alone at 5 μg/mL (in the presence of BSA) results in about 95% cell killing by 45 minutes while BPI protein at 1 μg/mL, which is sufficient in the absence of BSA to achieve cell killing of 95% at 45 minutes, never achieved higher than about 75% killing when plated on BSA supplemented agar. By comparison, the combination of rLBP and $rBPI_{23}$ resulted in approximately 95% cell killing by 90 minutes. Thus, LBP potentiated the irreversible bactericidal effect of $rBPI_{23}$ at a concentration of 1 ng/mL BPI. The incubation of cells with rLBP alone only caused a slight (25%) reduction in CFU relative to the control, although there did not seem to be evidence of cell division by 90 minutes with these cells as there was in the buffer-treated control. The results for plating on the BSA-supplemented nutrient agar, demonstrated that LBP potentiates the late, irreversible stage of BPI action. It is noted that while the LBP/BPI protein combination ultimately achieved the same degree of killing as $rBPI_{23}$ alone at 5 μg/mL (approximately 98%), it took longer to reach this level, requiring about 90 minutes versus 45 minutes for the BPI protein alone. This suggests that the cell killing kinetics for the LBP-potentiated BPI may be slower than for rBPI alone.

EXAMPLE 6

LBP Protein Product Potentiation of BPI Protein Product Bactericidal Activity in a Plate Assay

Figure 19:
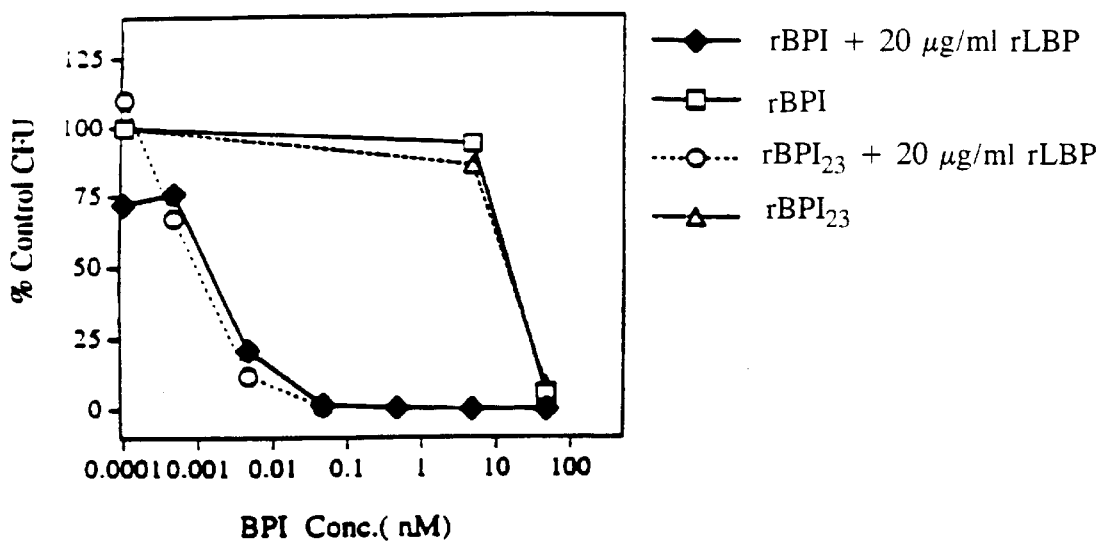
FIG. 19 depicts the results of a plate growth bactericidal assay with rBPI, $rBPI_3$, rLBP and combinations thereof.
Figure 20:
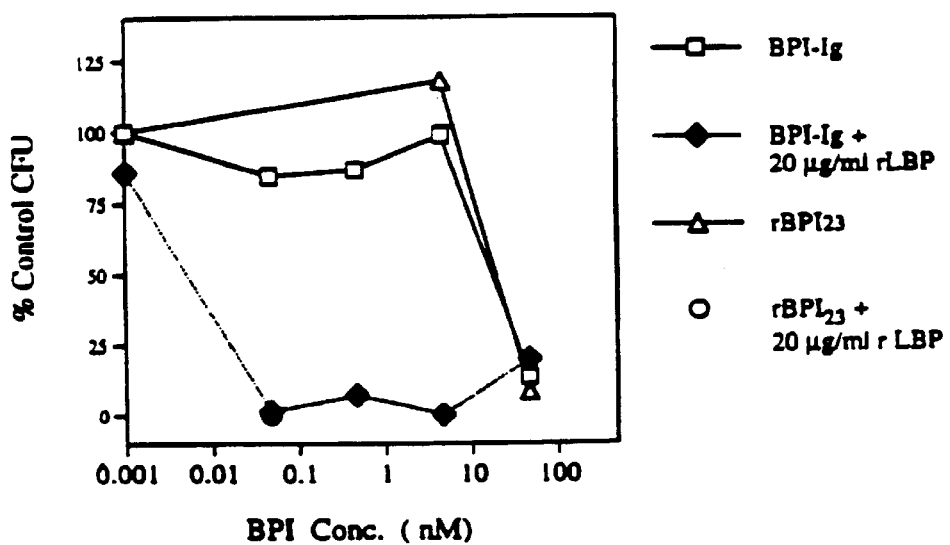
FIG. 20 depicts the results of a plate growth bactericidal assay with a recombinant BPI-Ig fusion protein [BPI-191/Hinge-$CH_2CH_3$], $rBPI_{23}$ rLBP and combinations thereof.
Figure 21:
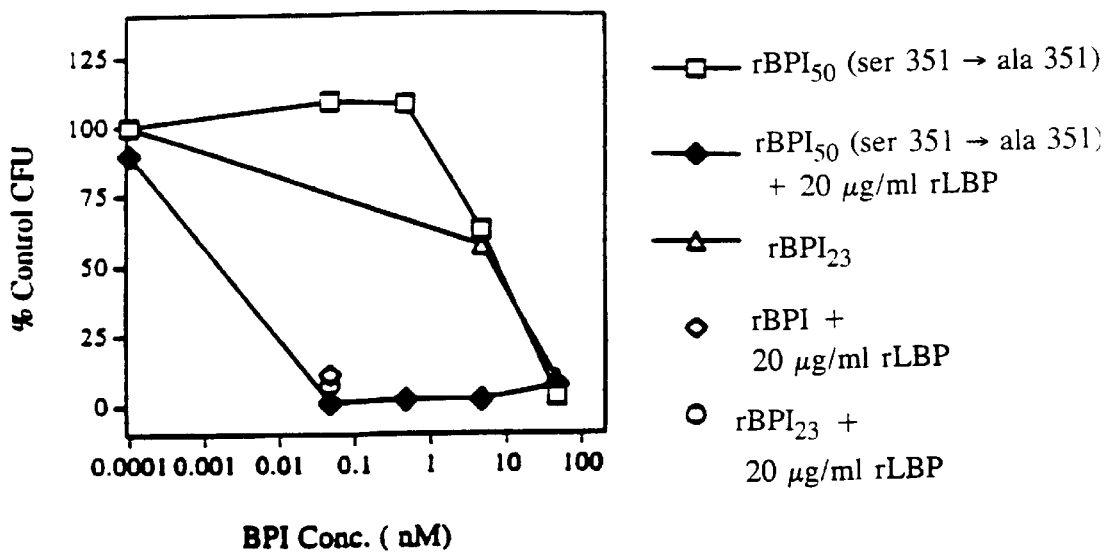
FIG. 21 depicts the results of a plate growth bactericidal assay with $rBPI_{50}$ (ser 351 ala 351), $rBPI_{23}$, rBPI rLBP and combinations thereof.
Figure 22:
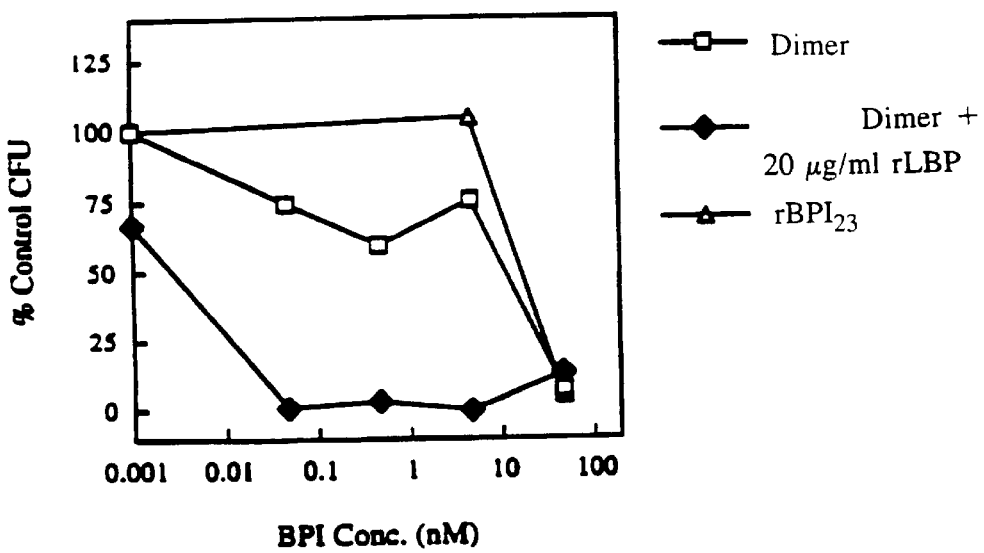
FIG. 22 depicts the results of a plate growth bactericidal assay with a recombinant dimeric form of an N-terminal BPI fragment (BPI dimer)
Figure 23A:
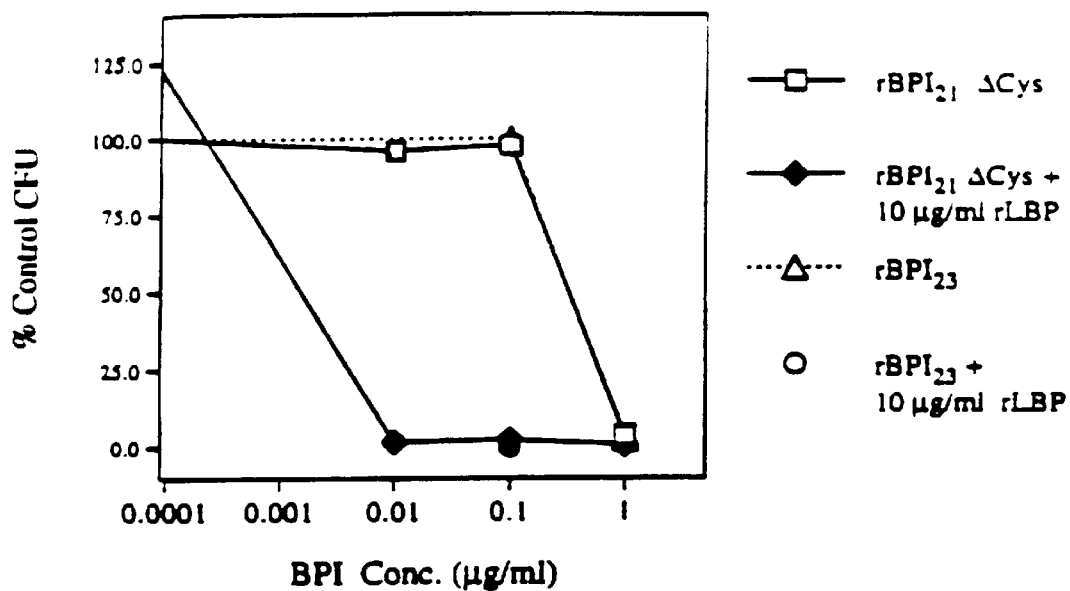
FIGS. 23 a and b depicts the results of a plate growth bactericidal assay with $rBPI_{21}\Delta cys$, $rBPI_{23}$ rLBP and combinations thereof.
Figure 23B:
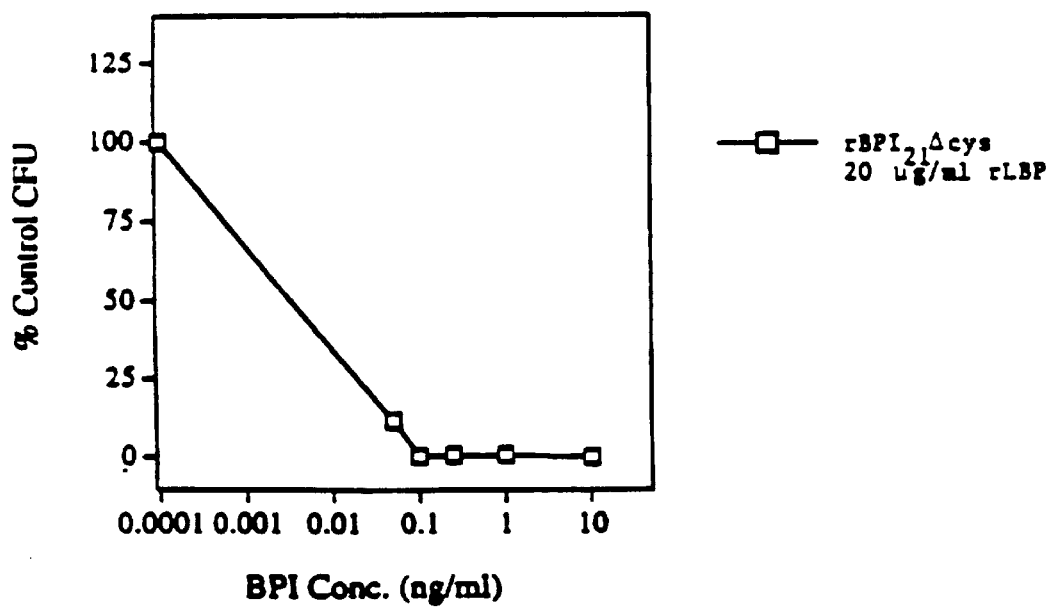

*E. coli* plate growth bactericidal assays as described in Example 2 were conducted utilizing rLBP with a variety of BPI protein products including a recombinant BPI holoprotein [$rBPI_{50}$], a recombinant N-terminal fragment of BPI [$rBPI_{23}$]. a recombinant BPI-Ig fusion protein [BPI-191/Hinge-$CH_2CH_3$], a recombinant variant of BPI holoprotein in which a single glycosylation site has been changed (ser 351 ala 351), a recombinant dimeric form of an N-terminal BPI fragment, and a recombinant analog of an N-terminal BPI fragment in which a cysteine residue has been changed (cys 132→ala 132) $rBPI_{21}\Delta cys$ with the results shown in FIGS. 19 through 23 below. FIG. 19 shows the results with recombinant rBPI holoprotein, rBPI. In FIG. 19, the data depicted as follows: rBPI with 20 μg/mL rIBP, —◆—; rBPI alone, —□—; $rBPI_{23}$ with 20 μg/mL rLBP, —○—; and $rBPI_{23}$ alone, —Δ—. FIGS. 19, 20 and 21 show the results with a recombinant N-terminal fragment of BPI, $rBPI_{23}$. FIG. 20 shows the results with a recombinant BPI-Ig fusion protein comprising N-terminal BPI (1–191) and the hinge, $CH_2$ and $CH_3$ constant domains of an immunoglobulin heavy chain according to U.S. patent application Ser. No. 08/064,693 filed May 19, 1993, now U.S. Pat. No. 5,643,570 which is a continuation-in-part of U.S. patent application Ser. No. 07/885,911 filed May 19, 1992, now abandoned and referred to in the specification of the pending application. In FIG. 20 the data are depicted as follows: BPI-Ig fusion protein product alone, —□—; the BPI-Ig fusion protein product with 20 μg/mL rLBP, —◆—; $rBPI_{23}$ alone, —Δ—; and $rBPI_{23}$ with 20 μg/mL rLBP, —○—. FIG. 21 shows the results with a recombinant variant of BPI holoprotein in which a single glycosylation site has been removed (ser 351→ala 351). In FIG. 21 the data are depicted as follows: $rBPI_{50}$ (ser 351→ala 351) alone, —□—; $rBPI_{50}$ (ser 351→ala 351) with 20 μg/mL rLBP, —◆—; $rBPI_{23}$, —Δ—; rBPI with 20 μg/mL rLBP, ◇; and $rBPI_{23}$ with 20 μg/mL rLBP, ○. FIG. 22 shows the results with a recombinant dimeric form of an N-terminal BPI fragment produced according to the methods of U.S. patent application Ser. No. 08/212,132 filed Mar. 11, 1994 now U.S. Pat. No. 5,447,913. In FIG. 22 the data are depicted as follows: BPI dimer, —□—; BPI dimer with 20 μg/mL rLBP, —◆—; and $rBPI_{23}$, —Δ—. FIGS. 23a and b show the results with a recombinant analog of an N-terminal BPI fragment (in which a cysteine residue has been changed (cys 132→ala 132), $rBPI_{21}\Delta cys$, which is described in co-owned, copending U.S. patent application Ser. No. 08/013.801 filed Feb. 2, 1993. In FIG. 23a the data are depicted as follows: $rBPI_{21}\Delta cys$ alone, —□—; $rBPI_{21}\Delta cys$ with 10 μg/mL rLBP, —◆—; $rBPI_{23}$ alone, —Δ—; and $rBPI_{23}$ with 10 μg/mL rLBP, ○. In FIG. 23b, the data are depicted as follows: $rBPI_{21}\Delta cys$ with 20 μg/mL rLBP, —□—. These results demonstrate that the bactericidal properties of each of the exemplified BPI protein products are potentiated by the addition of rLBP.

EXAMPLE 7

LBP Potentiation of BPI Permeabiuzation Activity with Actinomycin D

The effect of LBP proteins on the permeability increasing properties of BPI was determined. *E. coli* J5 bacteria were grown overnight in TYE broth and then a 1/200 dilution was subcultured in TEA medium. Bacteria were harvested at mid-logarithmic phase, suspended at about $8 \times 10^8$ cells/mL in sterile physiological saline and diluted 20-fold in a bactericidal assay medium consisting of 10% Hanks' balanced salts solution, 40 mM Tris-HCl (pH 7.4), 0.1% casamino acids, 0.9% NaCl and 0.4 mg/mL BSA (final cell density, about $4 \times 10^7$ cells/mL). Cells at about $4 \times 10^7$ cells/mL were mixed in a total volume of 200 µL with various concentrations of $rBPI_{23}$ with or without 20 µg/mL rLBP followed by 50 µg/mL actinomycin D (Sigma). As a control, the same experiment was performed without the actinomycin D. Following a 10 minute incubation at 37° C., the cells were diluted in sterile physiological saline containing 4 mg/mL BSA and plated on nutrient agar containing 0.9% NaCl and 1 mg/mL BSA.

Figure 24:
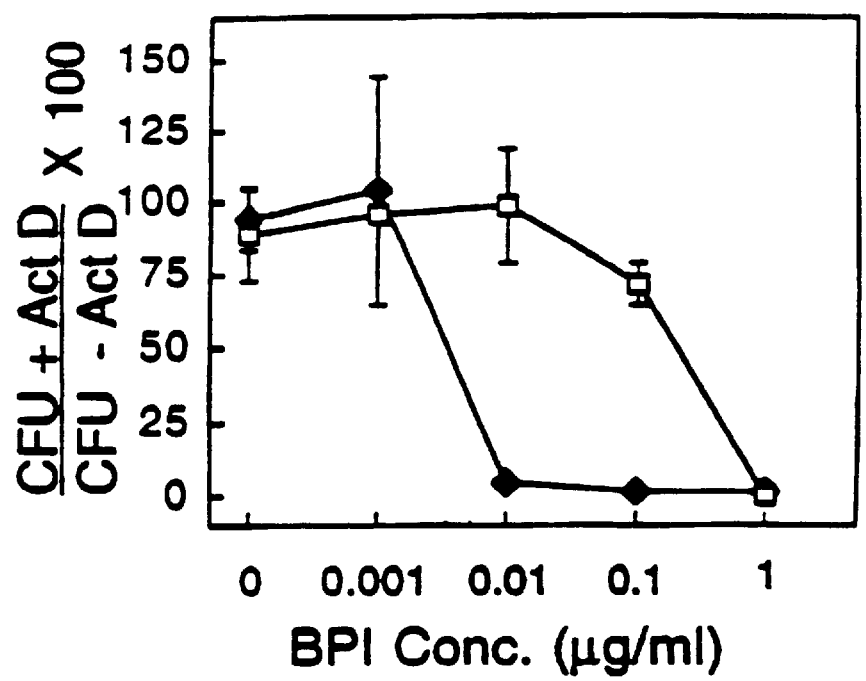
FIG. 24 depicts the results of Actinomycin D permeability assays utilizing rBPI$_{23}$, with and without rLBP.

The results are shown in FIG. 24 show that under these conditions, cells are protected by serum albumin from direct effects of BPI but not from the combined effects of BPI plus actinomycin D. In FIG. 24 Actinomycin D—assisted killing was the ratio of (CFU+ActD/CFU-ActD)×100 determined for each concentration in the assay. The results represent an average of three separate experiments with $rBPI_{23}$ alone, (—□—); rLBP plus $rBPI_{23}$, (—♦—). Treatment of cells with 1 µg/mL of $rBPI_{23}$ plus actinomycin D caused a reduction in CFUs of >95% on serum albumin-supplemented agar relative to treatment with $rBPI_{23}$ alone. Lower concentrations of $rBPI_{23}$ did not substantially facilitate actinomycin D-assisted killing and actinomycin D alone was not bactericidal in this assay. Addition of 20 µg/mL rLBP reduced by almost 100-fold the $rBPI_{23}$ concentration required to achieve approximately 95% actinomycin D-assisted killing, though rLBP alone did not permeabilize cells to actinomycin D. These results confirm that rLBP also potentiates the initial stage of $rBPI_{23}$ activity.

EXAMPLE 8

LBP Potentiation of BPI Activity in a Protein Synthesis Assay

Figure 25A:
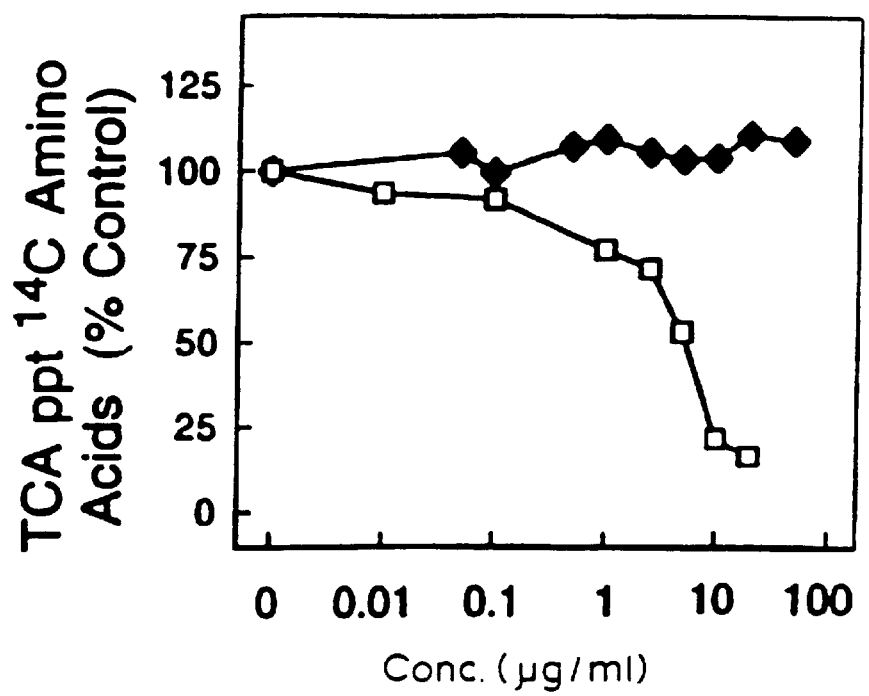
FIGS. 25a and b depict the results of rLBP and rBPI$_{23}$ in a protein synthesis assay.
Figure 25B:
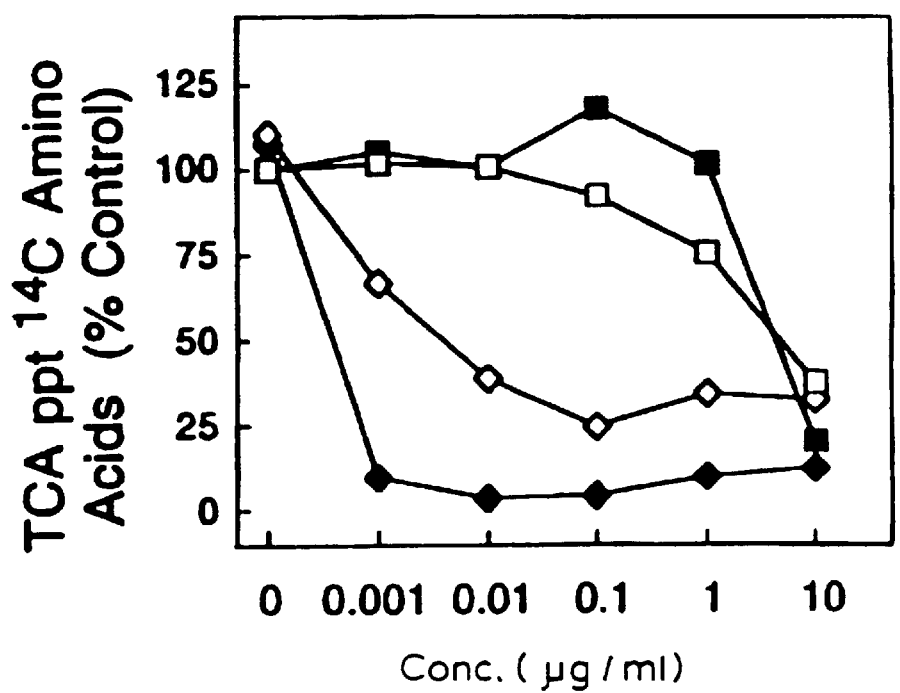

The effect of BPI and LBP on protein synthesis was assessed for *E. coli* J5 cells. The bacteria cells were grown overnight in TYE broth and then a 1/200 dilution was subcultured in TEA medium. Bacteria were harvested at mid-logarithmic phase, suspended at about $8 \times 10^8$ cells/mL in sterile physiological saline and diluted 20-fold in a bactericidal assay medium consisting of 10% Hanks' balanced salts solution, 40 mM Tris-HCl (pH 7.4), 0.1% casamino acids. and 0.9% NaCl (final cell density, about $4 \times 10^7$ cells/mL). The cells were incubated at 37° C. for 45 or 90 minutes with $rBPI_{23}$, rLBP or $rBPI_{23}$ plus rLBP in the bactericidal assay medium before 0.4 µCi of $^{14}$C-amino acids (New England Nuclear, Boston Mass.) was added and incubation was continued for an additional 20 minutes at 37° C. Incorporation of the $^{14}$C-amino acids was linear as a function of time for at least 20 minutes. Cells were treated with 3 mL of cold 10% trichloroacetic acid to arrest protein synthesis and release free $^{14}$C-amino acids from cells which were then applied to a 0.45 µM HA Millipore filter, washed once with 3 mL 10% trichloroacetic acid and then with 5 mL water. The filters were dried and counted in 10 mL of scintillation cocktail (Ready Flow III™. Beckman Instruments, Fullerton, Calif.) in a Beckman 7500™ scintillation counter with the results shown in FIGS. 25a and 25b. In FIG. 25a the effect of $rBPI_{23}$ (—□—) and rLBP (—♦—) alone on protein synthesis is shown. In FIG. 25b the effect of treatment with $rBPI_{23}$ alone (—■— and —□—, with the —□— representing treatment for 45 minutes and the —■— representing treatment for 90 minutes), and rLBP at 20 µl/mL plus $rBPI_{23}$ (—◊— and —♦—, with the —◊— representing treatment for 45 minutes and the —♦— representing treatment for 90 minutes) is shown.

These results show that treatment with BPI ultimately leads to impairment of protein synthesis as measured by incorporation of radiolabeled amino acids into an acid precipitable, cell-associated state. The results demonstrate that while rLBP alone at concentrations up to 50 µg/mL had no effect on protein synthesis (FIG. 25a), rLBP at 20 µg/mL enhanced $rBPI_{23}$ nediated inhibition of protein synthesis by about 1000-fold following a 45 minute incubation and 10,000-fold following a 90 minute incubation (FIG. 25b).

EXAMPLE 9

Potentiation of BPI Bactericidal Activity by an LBP/BPI Hybrid in a Plate Assay The effect of an LBP/BPI hybrid molecule on the bactericidal effect of $rBPI_{23}$ in a plate assay was determined. A plasmid encoding the LBP(1–197)BPI(200–456) hybrid was constructed by combining appropriate portions of the two molecules via a ClaI restriction site engineered into homologous locations in the DNA encoding the two molecules. The first step necessary for the construction of the mammalian expression vector pING4160 was the construction of two intermediate plasmids to introduce a ClaI restriction site by overlap extension PCR mutagenesis at the Ile-Asp at positions 197–198 in LBP (to generate plasmid pML127) and the Ile-Asp at positions 199–200 in BPI(to generate plasmid pML126). These were silent mutations which changed the nucleotide sequence only and not the amino acid sequence. The next step was to combine the amino terminal portion of LBP from pML127 with the carboxyl terminal of BPI from pML126 at the homologous ClaI sites to generate the intermediate plasmid pML128. The final step was then to subclone the LBP-BPI insert from pML126 into a mammalian expression vector to generate pING4160.

To construct plasmid pML127 (LBP with ClaI at 197–198). overlapping primers were designed to incorporate the changes necessary to encode a ClaI recognition site at the desired location. The template was pML125, a plasmid containing an insert encoding full length LBP. The primers were LBP-10, SEQ. ID. NO: 7, and LBP-8. SEQ. ID. NO: 8 facing downstream, and LBP-11, SEQ. ID. NO: 9 and LBP-Bsm, SEQ. ID. NO: 10 facing upstream. Two separate PCR reactions were carried out with primer pairs LBP-Bsm and LBP-11, to generate a 600 bp fragment that was then digested with StuI and ClaI to generate a 389 bp fragment, and primer pairs LBP-10 and LBP-8, to generate a 328 bp fragment that was then digested with ClaI and Bsu36I to generate a 148 bp fragment. The two resulting fragments were then ligated to the Bsu36I-StuI vector fragment from pML125 to generate the plasmid pML127.

To construct plasmid pML126 (BPI with ClaI at 199–200), overlapping primers were designed to incorporate the changes necessary to encode a ClaI recognition site at the desired location. The template was pML124, a plasmid containing an insert encoding full length BPI. The primers were BPI-63, SEQ. ID. NO: 11 and BPI-7, SEQ. ID. NO: 12 facing downstream, and BPI-64, SEQ. ID. NO: 13, and BPI-40, SEQ. ID. NO: 14, facing upstream. Two separate PCR reactions were carried out with primer pairs BPI-40 and BPI-64, to generate a 260 bp fragment that was then digested with PrnII and ClaI to generate a 170 bp fragment, and primer pairs BPI-7 and BPI-63, to generate a 296 bp fragment that was then digested with ClaI and BstXI to generate a 215 bp fragment. The two resulting fragments were then ligated to the BstXI-PmlI vector fragment from pML124 to generate the plasmid pML126.

To construct pML128, the intermediate plasmid encoding the LBP(1–197)BPI(200–456) hybrid, the 620 bp HindIII- ClaI fragment encoding the amino terminal region of BPI in the plasmid pML126 was replaced with the corresponding HindIII-ClaI fragment from pML127 encoding the amino terminal region of LBP.

To construct the mammalian expression vector pING4160. the 623 bp FspI-Bsu36I fragment of pML128 was ligated to the 361 bp SaU-FspI fragment from pING4539. (described in Gazzano-Santaro et al., U.S. application Ser. No. 08/261,660 filed Jun. 17. 1994) which includes the LBP signal sequence, and the approximately 8630 bp Bsu36I-SalI fragment from pING4321. The latter fragment includes sequences encoding part of the carboxyl terminus of BPI and all the vector sequences, which include the CMV promoter and the light chain 3' transcription termination sequences (as described in Ammons et al., U.S. application Ser. No. 08/212,132, filed Mar. 11, 1994).

To obtain the protein, beads co-cultured with CHO-K1 cells transfected with pING 4160 were washed with approximately 600 mls of 20 mM sodium acetate, pH 4.0 mM NaCl and then 600 mls of the same buffer containing 600 mM NaCl. Protein was eluted in two steps of 20 mM sodium acetate; the first with 1.0 M NaCl and the second with 1.5 M NaCl, with the majority of the desired protein eluting from the S-Sepharose in the 1.0 M step. Fractions containing the protein were then pooled and diluted to a final NaCl concentration of 300 mM with the addition of MES buffer, to a final concentration of 20 mM MES, pH 5.0. The diluted material recovered from all cell harvests was combined, yielding a final volume of approximately 6.5 liters. This pooled eluate was applied to two columns arranged in a tandem fashion, the first being a 100 ml Q-Sepharose column and the second a 12 ml CM-Spherodex column. The flow through material, which contained the desired protein, was adjusted to pH 4.0 and loaded in three batches on to a 15 ml S-Sepharose column. Each time the column was washed with 20 mM MES, pH 4.0 200 mM NaCl and the bound protein recovered with a step elution of 20 mM MES, pH 5.5, 1.2 M NaCl. The volume of the recovered protein was approximately 40 mls. This material was then run on a S-100 size exclusion column in 5 mM sodium citrate, pH 5.0, 150 mM NaCl. Column fractions were assayed using Coommassie stained SDS-PAGE and Western analysis using an anti-LBP primary antibody. P4160 fractions containing the protein LBP (1–197)BPI(200–456).

Figure 26:
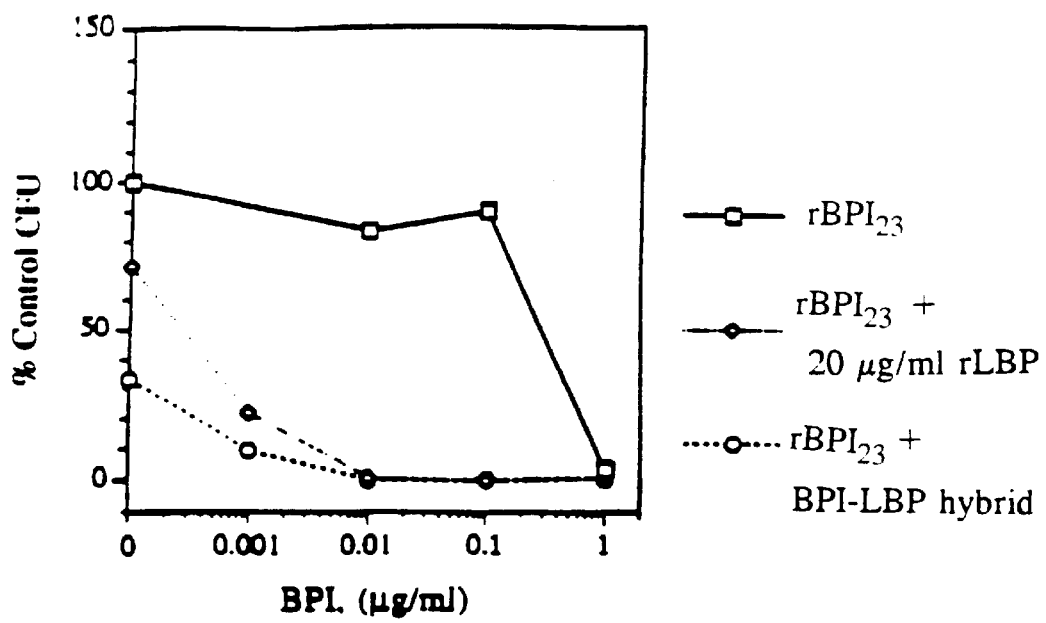
FIG. 26 depicts the results of a plate growth bactericidal assay with rBPI$_{23}$ in combination with either rLBP or an LBP/BPI hybrid protein (LBP(1–197)/BPI(200–456)

Specifically, an *E. coli* plate growth assay was carried out according to the general method of Example 2 using rBPI$_{23}$, rBPI$_{23}$ in combination with 20 µg/mL rLBP, and rBPI$_{23}$ in combination with 20 µg/mL of an LBP/BPI hybrid designated LBP(1–197)/BPI(200–456) comprising the first 197 residues of LBP linked to amino acid residues 200–456 of BPI. The results illustrated in FIG. 26 wherein the results with rBPI$_{23}$ alone are depicted by —□—, the results with rBPI$_{23}$ in combination with 20 µg/mL rLBP are depicted by —◇—, and the results with rBPI$_{23}$ in combination with 20 µg/mL LBP/BPI hybrid are depicted by —○— show that both rLBP and the LBP/BPI hybrid potentiate the bactericidal effect of rBPI$_{23}$.

EXAMPLE 10

Effect of Order of Addition of BPI and LBP in a Plate Bactericidal Assay

The effect of order of addition of BPI and LBP protein products in a plate bactericidal assay was determined by varying the order of addition of the protein products and incubating cells in the presence of only one of the protein products prior to contacting with the second protein product. Specifically *E. coli* J5 cells were grown up according to the method of Example 2 and the bactericidal assays were conducted according to the methods of that example. rBPI$_{23}$ was used at a concentration of 1 ng/mL while rLBP was administered at 20 µg/mL. According to the "normal" condition such as practiced in Example 2 above, one of the protein products was added and was followed by the other protein product within the first 2–3 minutes. Alternatively, one of the protein products was added to the cells which were allowed to incubate for 15 or 40 minutes prior to addition of the other protein product. The total incubation time was 45 minutes for all samples, thus the incubation period with both the BPI and LBP protein products present was 45, 30 or 5 minutes.

Figure 27:
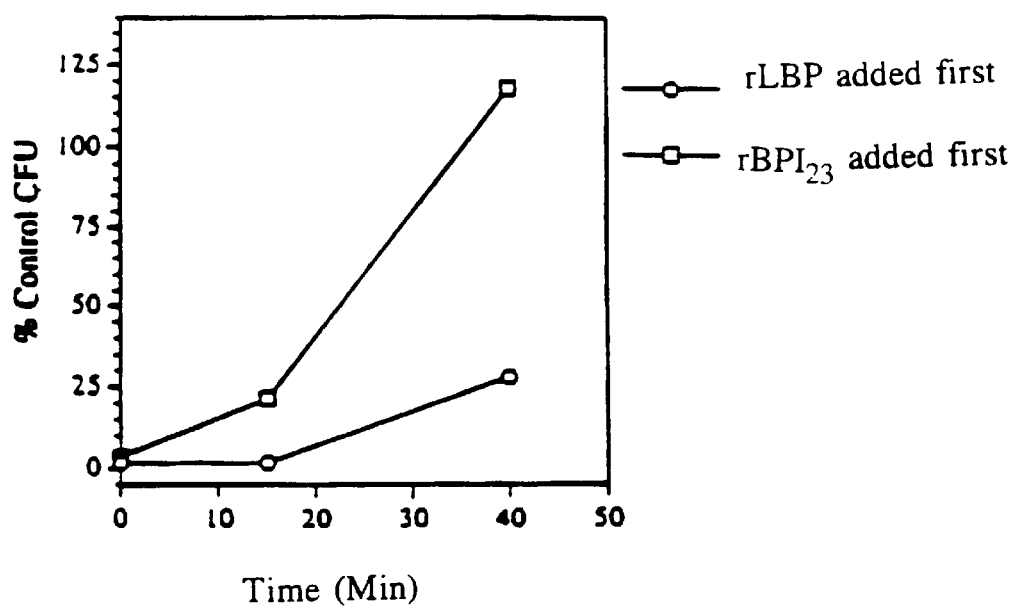
FIG. 27 depicts the results of a plate growth bactericidal assay examining the effect of order of addition of rBPI$_{23}$ and rLBP on potentiation of BPI bactericidal activity.

The results are shown in FIG. 27 wherein the experiments in which rLBP was added first are depicted by (—○—) and the experiments in which rBPI$_{23}$ was added first are depicted by (—□—) with the results at time 0 being those experiments in which both protein products were added essentially simultaneously. These results suggest that pre-treatment of cells with LBP protein products sensitize them to bactericidal action by a small number of BPI molecules even if the BPI protein product is added to the cells 15 or 40 minutes after the LBP protein product. In contrast, pre-treatment with a low concentration of a BPI protein product is progressively less effective as a function of time. For example, a 40 minute pretreatment with rBPI$_{23}$ followed by a 5 minute incubation with rLBP results in no bactericidal effect.

Without being bound by a theory of action, it is noted that these results are consistent with the model whereby LBP protein products function by occupying the large number of available LPS sites on the outer membrane surface that are normally bound by the majority of BPI molecules. Binding of LBP (or an excess of BPI) to these sites could promote subsequent interaction of a small number of BPI molecules at a second class of sites at or below the outer membrane surface leading ultimately to growth arrest and cell death. Such a model might suggest that addition of low concentrations of BPI first could cause interaction of BPI at sites that do not result in lethal action. Incubation with LBP first, however, would provide full occupancy of these sites allowing BPI to interact with sites leading to lethal action.

Numerous modifications and variations in the practice of the invention are expected to occur to those skilled in the art upon consideration of the foregoing description of the presently preferred embodiments thereof. Consequently, the only limitations which should be placed upon the scope of the present invention are those which appear in the appended claims.

What is claimed is:

1. A method of treating a gram-negative bacterial infection in a subject comprising administering to said subject a bactericidal/permeability-increasing protein (BPI) protein product a lipopolysaccharide binding protein (LBP) protein product and an antibiotic, in amounts effective to treat the gram-negative bacterial infection.

2. The method of claim 1 wherein the LBP protein product is administered in an amount effective to potentiate the bactericidal properties of said BPI protein product.

3. The method of claim 1 wherein the LBP protein product is an amino-terminal LBP fragment.

4. The method of claim 1 wherein the LBP protein product is characterized by a molecular weight of about 25 kD.

5. The method of claim 1 wherein the LBP protein product is rLBP.

6. The method of claim 1 wherein the proteins are administered systemically.

7. The method of claim 1 wherein the proteins are administered topically.

8. A method of killing gram-negative bacteria comprising administering to said bacteria a BPI protein product in combination with an LBP protein product and an antibiotic, in amounts effective to kill the gram-negative bacteria.

9. The method of claim 8 wherein said BPI protein product and said LBP protein product are administered in vivo.

10. The method of claim 8 wherein said BPI protein product and said LBP protein product are administered in vitro.

11. The method of claim 8 wherein the LBP protein product is an amino-terminal LBP fragment.

12. The method of claim 8 wherein the LBP protein product is characterized by a molecular weight of about 25 kD.

13. The method of claim 8 wherein the LBP protein product is LBP.

14. A pharmaceutical composition for treatment of gram-negative bacterial infection comprising a BPI protein product an LBP protein product and an antibiotic, in amounts effective to treat the gram-negative bacterial infection.

15. The pharmaceutical composition of claim 14 comprising a pharmaceutically-acceptable diluent, adjuvant, or carrier.

16. The pharmaceutical composition of claim 14 wherein the LBP protein product is an amino-terminal LBP fragment.

17. The pharmaceutical composition of claim 14 wherein the LBP protein product is characterized by a molecular weight of about 25 kD.

18. A gram-negative cytotoxic composition comprising a BPI protein product, an LBP protein product and an antibiotic, in amounts effective to kill gram-negative bacteria.

19. The method of claim 1 wherein the LBP protein product is LBP(1–197)/BPI(200–456) hybrid.

20. The method of claim 8 wherein the LBP protein product is LBP (1–197)/BPI(200–456) hybrid.

21. The pharmaceutical composition of claim 14 wherein the LBP protein product is LBP(1–197)/BPI(200–456) hybrid.

* * * * *

UNITED STATES PATENT AND TRADEMARK OFFICE
CERTIFICATE OF CORRECTION

PATENT NO.    : 6,051,553
DATED         : April 18, 2000
INVENTOR(S)   : Arnold Horwitz It is certified that error appears in the above-identified patent and that said Letters Patent is hereby corrected as shown below:

Column 39, claim 1,
Line 17, insert a comma after "(BPI) protein product". See Amendment mailed 3/15/99.

Column 40, claim 14,
Line 21, insert a comma after "BPI protein Product." See Amendment mailed 3/15/99.

Signed and Sealed this

Twelfth Day of March, 2002

Attest:

JAMES E. ROGAN
Attesting Officer   Director of the United States Patent and Trademark Office